US012788825B2

(12) United States Patent
Hopkins et al.

(10) Patent No.: US 12,788,825 B2
(45) **Date of Patent: *Nov. 10, 2026**

(54) NANOPARTICLES FOR USE IN PHOTODYNAMIC THERAPIES AND METHODS OF MAKING, EVALUATING AND USING THE SAME

(71) Applicant: Kuva Labs Inc., Houston, TX (US)

(72) Inventors: Andrew Hopkins, Houston, TX (US); Thomas Hopkins, Houston, TX (US)

(73) Assignee: Kuva Labs Inc., Houston, TX (US)

( * ) Notice: Subject to any disclaimer, the term of this patent is extended or adjusted under 35 U.S.C. 154(b) by 320 days.

This patent is subject to a terminal disclaimer.

(21) Appl. No.: 18/738,951

(22) Filed: Jun. 10, 2024

(65) Prior Publication Data

US 2024/0325566 A1 Oct. 3, 2024

Related U.S. Application Data

(63) Continuation of application No. 17/228,332, filed on Apr. 12, 2021, now Pat. No. 12,005,125.

(60) Provisional application No. 63/008,653, filed on Apr. 10, 2020.

(51) Int. Cl.

| | |
|---|---|
| ***A61K 47/69*** | (2017.01) |
| ***A61K 41/00*** | (2020.01) |
| ***A61K 47/64*** | (2017.01) |
| *B82Y 5/00* | (2011.01) |
| *B82Y 30/00* | (2011.01) |
| *B82Y 40/00* | (2011.01) |

(52) U.S. Cl.

CPC ...... *A61K 47/6935* (2017.08); *A61K 41/0071* (2013.01); *A61K 47/64* (2017.08); *B82Y 5/00* (2013.01); *B82Y 30/00* (2013.01); *B82Y 40/00* (2013.01)

(58) Field of Classification Search

CPC ............ A61K 47/6935; A61K 41/0071; A61K 47/64; A61K 47/62; B82Y 5/00; B82Y 30/00; B82Y 40/00

See application file for complete search history.

(56) References Cited

U.S. PATENT DOCUMENTS

| | | | |
|---|---|---|---|
| 7,005,518 | B2 | 2/2006 | Peng |
| 8,562,944 | B2 | 10/2013 | Pandey |
| 8,906,343 | B2 | 12/2014 | Pandey |
| 9,045,488 | B2 | 6/2015 | Pandey |
| 9,115,110 | B2 | 8/2015 | Frey |
| 10,370,245 | B2 | 8/2019 | Ruoslahti |
| 12,005,125 | B2 | 6/2024 | Hopkins |
| 2009/0226372 | A1 | 9/2009 | Ruoslahti |
| 2009/0246133 | A1 | 10/2009 | Ruoslahti |
| 2009/0326434 | A1 | 12/2009 | Nifantiev |
| 2012/0071810 | A1 | 3/2012 | Cooper |
| 2015/0328315 | A1 | 11/2015 | Kalifa |
| 2018/0250405 | A1 | 9/2018 | Biel |
| 2020/0101176 | A1 | 4/2020 | Hopkins |
| 2021/0085790 | A1 | 3/2021 | Hopkins |

OTHER PUBLICATIONS

An updated overview on the development of new photosensitizers for anticancer photodynamic therapy, Zhang et al., published Sep. 22, 2017.

New photosensitizers for photodynamic therapy, Abrahamse et al., published Feb. 15, 2016.

Basic Photosensitization, Nancy L. Oleinick, accessed Aug. 17, 2021.

Photocatalytic generation of oxygen radicals by the water-soluble bacteriochlorophyll derivative WST11, noncovalently bound to serum albumin, Ashur et al., published Jul. 16, 2009.

Photodynamic therapy: current status and future directions, Ludmil Benov, published May 10, 2014.

Tumor cell survival pathways activated by photodynamic therapy: a molecular basis for pharmacological inhibition strategies, Broekgaarden et al., published Oct. 29, 2015.

Mechanisms of Resistance to Photodynamic Therapy, Casas et al., available Sep. 23, 2013.

Photophysics and photochemistry of photodynamic therapy: fundamental aspects, Plaelzer et al., published Feb. 5, 2008.

Sensitivity of photoacoustic microscopy, Yao et al., published Apr. 14, 2014.

Nano-photosensitizers Engineered to Generate a Tunable Mix of Reactive Oxygen Species, for Optimizing Photodynamic Therapy, Using a Microfluidic Device, Yoon et al., published Feb. 25, 2014.

Physical-Chemical Study of Anthracene Selective Oxidation by a Fe(III)-Phenylporhyrin Derivative, Diaz-Uribe et al., Published Jan. 5, 2020.

Production of singlet oxygen by Ru(dpp(SO3)2)3 incorporated in polyacrylamide PEBBLES, Moreno et al., published Apr. 20, 2003.

Cell-selective arrhythmia ablation for photomodulation of heart rhythm, Avula et al., published Oct. 28, 2015.

Ultracompact Nanotheranostic PEG Platform for Cancer Applications, Hopkins et al., accessed Aug. 17, 2021.

Drug resistance and the solid tumor microenvironment, Tredan et al., published Oct. 3, 2007.

Handbook of Photodynamic Therapy—Updates on Recent Applications of Porphyrin-Based Compounds, Ravindra K Pandey, Jun. 2016.

(Continued)

*Primary Examiner* — Robert S Cabral

(74) *Attorney, Agent, or Firm* — Choate, Hall & Stewart LLP; Brenda Herschbach Jarrell

(57) ABSTRACT

A nanocomposition for use in treating cardiac, oncologic, bariatric, or dermatologic indications, conditions and diseases condition using phthalocyanine dye, such as IR700. A nanocomposition having IR700, an 8PEG nanoparticle and a RGD, or iRGD targeting agent. Administering a product comprising IR700 to a patient, whereby the IR700 is delivered to the target tissue, and found in only target tissue; and administering light to activate the IR700, thereby producing an ROS.

22 Claims, 10 Drawing Sheets

(56) References Cited

OTHER PUBLICATIONS

International Search Report and Written Opinion for Application No. PCT/US2021/026923, dated Jul. 16, 2021.
Multiarm Nanoconjugates for Cancer Cell-Targeted Delivery of Photosensitizers, Zhao et al., Published May 16, 2018.

A)

NHS - PEG - MAL

SMCC

Thio propionic acid - NHS

Chloropropyne

B)

(1) (2)

PS – COOH "IR700DX"

"IR700DX SCM"

NANOPARTICLES FOR USE IN PHOTODYNAMIC THERAPIES AND METHODS OF MAKING, EVALUATING AND USING THE SAME

This application is a continuation of U.S. application Ser. No. 17/228,332 filed Apr. 12, 2021, which claims priority to and the benefit of U.S. Provisional Application No. 63/008,653 filed Apr. 10, 2020, the entire disclosure of which are incorporated herein by reference in their entirety.

BACKGROUND OF THE INVENTION

The present inventions relate generally to nanocompositions and uses of these compositions in dynamic therapies, imaging, diagnostics, theranostics and other applications.

The terms "nanocomposition", "nanoparticle", "nanomaterial", "nanoparticle", nanoproduct", "nanoplatform", "nanoconstruct", "nanocomposite", "nano", and similar such terms, unless specified otherwise, are to be given their broadest possible meaning, and include particles, materials and compositions having a volumetric shape that has at least one dimension from about 1 nanometer (nm) to about 100 nm. Preferably, in embodiments, these volumetric shapes have their largest cross section from about 1 nm to about 100 nm.

The terms "nanocomposition", "nanoconstructs", "nanoplatform", "nanocomposite", and "nanoconstruct" and similar such terms, unless specified otherwise, are to be given their broadest possible meaning, and include a particle having a backbone material, e.g., a cage, support or matrix material, and one or more additives, e.g., agents, moieties, compositions, biologics, and molecules, that are associated with the backbone. Generally, the backbone material can be a nanoparticle. Generally, the additive is an active material having targeting, therapeutic, imaging, diagnostic, theranostic or other capabilities, and combinations and variations of these. In embodiments, the backbone material can be an active material, having targeting, therapeutic, imaging, diagnostic, theranostic or other capabilities, and combinations and variations of these. In embodiments both the additive and the backbone material are active materials. One, two, three or more different types of backbone materials, additives and combination and variations of these are contemplated.

The term "theranostic", unless specified otherwise, is to be given its broadest possible meaning, and includes a particle, agent, composition, or material that has multiple capabilities and functions, including both imaging and therapeutic capabilities, both diagnostic and therapeutic capabilities, and combinations and variations of these and other features such as targeting.

The terms "imaging", "imaging agent", "imaging apparatus" and similar such terms, unless specified otherwise, should be given their broadest possible meaning, and would include apparatus, agents and materials that enhance, provide or enable the ability to detect, analyze and visualize the size, shape, position, composition, and combinations and variations of these as well as other features, of a structure, and in particular structures in animals, mammals and humans. Imaging agents would include contrast agents, dies, and similar types of materials. Examples of imaging apparatus and methodologies include: x-ray; magnetic resonance; computer axial tomography scan (CAT scan); proton emission tomography scan (PET scan); ultrasound; florescence; and, photo acoustic.

The term, "diagnostic", unless specified otherwise, is to be given its broadest possible meaning, and would include identifying, determining, defining and combinations and variations of these, conditions, diseases and both, including conditions and diseases of animals, mammals and humans.

The term "therapeutic" and "therapy" and similar such terms, unless specified otherwise, are to be given their broadest possible meaning and would include addressing, treating, managing, mitigating, curing, preventing, and combinations and variations of these, conditions and diseases, including conditions and disease of animals, mammals and humans.

The terms "photodynamic therapy", "PDT" and similar such terms, unless expressly stated otherwise, are to be given their broadest possible meaning and would include a method for ablating, (e.g., killing, destroying, rendering inert), biological tissue by photo-oxidation utilizing photosensitizer ("PS") molecules. When the photosensitizer is exposed to a specific wavelength or wavelengths of light, it produces a form of oxygen from adjacent (e.g., in situ, local, intercellular, intracellular) oxygen sources, that kills nearby cells, e.g., reactive oxygen species ("ROS"), which includes any form of oxygen that are cyto-toxic to cells. It being understood that while light across all wavelengths, e.g., UV to visible to IR, is generally used as the activator of the PS, PS typically have a wavelength, or wavelengths where their absorption is highest.

The terms "activation dynamic therapy", "dynamic therapy", "dynamic therapy agent" and similar such terms, unless expressly stated otherwise, should be given their broadest possible meaning and would include PDT and PS, as well as agents that are triggered to product active oxygen, such as a reactive oxygen species ("ROS") or other active therapeutic materials, when exposed to energy sources including energy sources other than light, as activators. These would include materials or agents that are activated by energy sources such as radio waves, other electromagnet radiation, magnetism, and sonic (e.g., Sonodynamic therapy or SDT).

The terms "photosensitizer" and "PS" and "photoactive agent" and similar such terms, unless expressly stated otherwise, should be given their broadest possible meaning and would include any dye, molecule or modality that when exposed to light produces, or causes the production of ROS, or other active agents that are cyto-toxic to cells, kill tissue, ablates tissue, destroys tissue or renders a pathogen inert.

The terms "targeting agent" and "TA" and similar such terms, unless expressly stated otherwise, should be given their broadest possible meaning and would include any molecule, material or modality that is targeted to, or specific for, or capable of binding to or with, a predetermined cell type, receptor, or pathogen. TA would include, for example, a protein, a peptide, an enzyme substrate, a hormone, an antibody, an antigen, a hapten, an avidin, a streptavidin, biotin, a carbohydrate, an oligosaccharide, a polysaccharide, a nucleic acid, a deoxy nucleic acid, a fragment of DNA, a fragment of RNA, nucleotide triphosphates, acyclo terminator triphosphates, peptide nucleic acid (PNA) biomolecules, and combinations and variations of these.

As used herein, unless expressly stated otherwise the term "pathogen" should be given its broadest possible means in would include any organism that can cause a disease or condition in animals (including humans, pets and livestock) or plants. Pathogens would include, for example, viruses, bacteria, fungi, molds, and parasites. Pathogens would include, for example, among others influenza viruses, corona viruses, COVID-19, SARS-COV-2, Ebola, HIV, SARS, H1N1 and MRSA.

The term "antibody" as used herein, unless specified otherwise, should be given its broadest possible meaning, and would include a polypeptide ligand comprising at least a light chain or heavy chain immunoglobulin variable region which specifically recognizes and binds an epitope of an antigen, such as a tumor-specific protein. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. Antibodies include intact immunoglobulins and the variants and portions of antibodies well known in the art, such as Fab fragments, Fab' fragments, $F(ab)'_2$ fragments, single chain Fv proteins ("scFv"), and disulfide stabilized Fv proteins ("dsFv"), A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook,* 1994-1995 (Pierce Chemical Co., Rockford, Ill.); Kuby, J., *Immunology,* 3rd Ed., W. H. Freeman & Co., New York, 1997. The term antibody would include monoclonal antibodies, chimeric antibodies, and humanized immunoglobulin, to name a few.

As used herein, unless stated otherwise, room temperature is 25° C. And, standard ambient temperature and pressure is 25° C. and 1 atmosphere. Unless expressly stated otherwise all tests, test results, physical properties, and values that are temperature dependent, pressure dependent, or both, are provided at standard ambient temperature and pressure, this would include viscosities.

Generally, the term "about" and the symbol "~" as used herein unless stated otherwise is meant to encompass a variance or range of ±10%, the experimental or instrument error associated with obtaining the stated value, and preferably the larger of these.

As used herein, unless specified otherwise, the recitation of ranges of values, a range, from about "x" to about "y", and similar such terms and quantifications, serve as merely shorthand methods of referring individually to separate values within the range. Thus, they include each item, feature, value, amount or quantity falling within that range. As used herein, unless specified otherwise, each and all individual points within a range are incorporated into this specification, and are a part of this specification, as if they were individually recited herein.

As used herein, unless expressly stated otherwise terms such as "at least," "greater than," also mean "not less than," i.e., such terms exclude lower values unless expressly stated otherwise.

This Background of the Invention section is intended to introduce various aspects of the art, which may be associated with embodiments of the present inventions. Thus, the forgoing discussion in this section provides a framework for better understanding the present inventions, and is not to be viewed as an admission of prior art.

SUMMARY

There has been a long-standing and unfulfilled need for new and innovative drugs, medical products and imaging agents to address conditions and diseases of animals, mammals and humans. In particular, this long-standing and unfulfilled need is present in, among others, cardiology, oncology, dermatology, and bariatrics, including for diagnoses and treatments.

The present inventions, among other things, solve these needs by providing the compositions, materials, articles of manufacture, devices, methods and processes taught, disclosed and claimed herein.

Thus, there is provided a nanocomposition having: a photosensitizer (PS), wherein the photosensitizer includes a phthalocyanine dye; a nanoparticle (NP); wherein the nanoparticle includes 8PEG; and, a targeting agent (TA), wherein the targeting agent includes a targeting peptide (TP).

There is further provided these methods, treatments, compositions, kits, and nanocompositions having one or more of the following features: wherein the nanocomposition is configured to provide a photodynamic therapy for a cardiac, oncologic, bariatric, or dermatologic indication; wherein the PS is IR700; the 8PEG is selected from the group constituting of 8PEGA and 8PEGMAL; wherein the PS is IR700; the 8PEG is selected from the group constituting of 8PEGA and 8PEGMAL, and wherein the PS is IR700; the 8PEG is selected from the group constituting of 8PEGA and 8PEGMAL, and having 3 and less PS per NP.

Moreover, there is provided a nanocomposition, for use in treating a cardiac, oncologic, bariatric, or dermatologic condition, the nanocomposition having: a photosensitizer (PS), wherein the photosensitizer is a phthalocyanine dye; a nanoparticle (NP); wherein the nanoparticle is selected from the group of 8PEG, 8PEGA and 8PEGMAL; and, a targeting agent (TA), wherein the targeting agent is a targeting peptide (TP) that is specific to the condition; wherein the nanocomposition is configured for providing a photodynamic therapy for the specific condition.

There is further provided these methods, treatments, compositions, kits, and nanocompositions having one or more of the following features: wherein the nanocomposition has less than 3 PS per NP.

Still further, there is provided a method of treating a cardiac, oncologic, bariatric, or dermatologic condition, using any of these nanocomposition, the method including: administering to an animal a plurality of any of any of these nanocompositions; waiting a sufficient time for the nanocompositions to accumulate in a targeted tissue of the animal; and, illuminating the targeted tissue with light having a wavelength and sufficient energy to activate the PS, thereby producing reactive oxygen species (ROS).

There is further provided these methods, treatments, compositions, kits, and nanocompositions having one or more of the following features: wherein the light is a laser beam; wherein the illumination of the targeted tissue results in less than a 10 degree C. raise in temperature of the illuminated tissue; wherein the illumination of the targeted tissue results in less than a 5 degree C. raise in temperature of the illuminated tissue; wherein the illumination of the targeted tissue results in less than a 2 degree C. raise in temperature of the illuminated tissue; wherein the illumination of the targeted tissue does not raise the temperature of the illuminated tissue; wherein the illumination of the targeted tissue does not result in thermal breakdown of the illuminated tissue; and wherein the illumination of the targeted tissue does not result in induced optical breakdown.

Yet additionally, there is provided a kit having a container having a plurality of the nanocompositions of any of these nanoparticles and an illumination light source having a wavelength and power selected to activate the PS.

There is further provided these methods, treatments, compositions, kits, and nanocompositions having one or more of the following features: wherein the illumination light includes a disposable optical delivery device, wherein the optical delivery device can be an optical fiber; wherein the optical device can an LED; and wherein the optical delivery device can be an array of LEDs.

Furthermore, there is provided a composition for use in treating a cardiac, oncologic, bariatric, or dermatologic condition using a photodynamic therapy, the composition having: a photosensitizer (PS), wherein the photosensitizer is a phthalocyanine dye; a core molecule; and, a targeting agent (TA), wherein the TA is specific to the targeted tissue.

There is further provided these methods, treatments, compositions, kits, and nanocompositions having one or more of the following features: wherein the composition is a nanocomposition and the core molecule is a nanoparticle NP; wherein the core molecule is selected from the group consisting of PEG, 8PEG, 8PEGA and 8PEGMAL; wherein the PS is water soluble; wherein the PS, TA and both are directly attached to the core molecule; wherein the direct attachment is a covalent bond; wherein the PS, TA and both are attached to the core by a linking moiety; wherein the TA is attached to the core by a linking moiety; wherein the TA is attached to the PS; wherein the TA is attached to the PS; and wherein the TA is not directly attached to the core; wherein the TA and PS form a conjugate, wherein the conjugate is attached to the core; wherein the core is an 8PEG nanoparticle, and the 8PEG nanoparticle has one free arm; wherein the core is an 8PEG nanoparticle, and the 8PEG nanoparticle has at least two free arms; wherein the core is an 8PEG nanoparticle, and the 8PEG nanoparticle has at least three free arms; wherein the core is an 8PEG nanoparticle, having no more than three PS; wherein the core is an 8PEG nanoparticle, having no more than two PS; wherein the core is an 8PEG nanoparticle, and a ratio of TA to PS is selected from the group consisting of and wherein the 2.5 to 1, 3 to 1, 4 to 1 and 5 to 1; wherein the core is an 8PEG nanoparticle, and wherein the composition has a hydrodynamic diameter selected from the group consisting of 70 nm and less, 50 nm and less, 25 nm and less, and 10 nm and less; and, wherein the core is an 8PEG nanoparticle, and wherein the nanoparticle has a mass selected from the group consisting of about 10 kDa and greater, about 20 kDa and greater, about 40 kDa and greater, and about 50 kDa and greater.

Yet further, there is provided a method of treating a cardiac, oncologic, bariatric, or dermatologic condition having: administering to an animal a targeted nanoparticle having IR700; wherein the nanoparticle has a targeting agent; delivering light in the wavelength range of from about 600 nm to about 800 nm to a targeted tissue having the target nanoparticle; whereby the IR700 is activated and the targeted tissue is destroyed.

There is further provided these methods, treatments, compositions, kits, and nanocompositions having one or more of the following features: wherein the animal is a mammal; wherein the animal is a human; wherein the nanoparticle is 8PEGA; wherein the targeting agent is a specific protein for the target tissue; wherein the targeting agent targets targeted cells, and whereby only the targeted cells are destroyed; wherein the targeting agent is a specific targeting peptide for the targeted cells.

Still further, there is provided treating a cardiac, oncologic, bariatric, or dermatologic condition using IR700.

Yet additionally, there is provided administering a targeted nanocomposition to a patient, the nanocomposition having IR700, a TP and an 8PEG nanoparticle, whereby the nanocomposition accumulated in a targeted tissue of the patient.

Moreover, there is provided, administering a product having IR700 to a patient, whereby the IR700 is delivered to targeted tissue, and found in only the targeted tissue; and administering light to activate the IR700, thereby producing an ROS.

Still further, there is provided a method of treating cardiac, oncologic, bariatric, or dermatologic tissue, the method including: contacting an animal with a nanoparticle having a matrix, an active agent, and a targeting moiety; and administering an activator of said active agent to at least a portion of the targeted tissue of said animal; wherein the active agent includes a phthalocyanine dye having a luminescent fluorophore moiety having at least one silicon containing aqueous-solubilizing moiety, wherein said phthalocyanine dye has a core atom selected from the group consisting of Si, Ge, Sn, and Al; wherein said phthalocyanine dye exists as a single core isomer, essentially free of other isomers; and has a reactive or activatable group.

Additionally, there is provided a method of treating cardiac, oncologic, bariatric, or dermatologic condition, comprising contacting an animal with a nanoparticle having a matrix, an active agent, and a targeting moiety; and administering an activator of said active agent to at least a portion of the targeted tissue of said animal; wherein the active agent consists essentially of a phthalocyanine dye having a luminescent fluorophore moiety having at least one silicon containing aqueous-solubilizing moiety, wherein said phthalocyanine dye has a core atom selected from the group consisting of Si, Ge, Sn, and Al; wherein said phthalocyanine dye exists as a single core isomer, essentially free of other isomers; and has a reactive or activatable group.

There is further provided these methods, treatments, compositions, kits, and nanocompositions having one or more of the following features: wherein the matrix includes PEG, and wherein the said core atom of the dye is Si.

There is further provided these methods, treatments, compositions, kits, and nanocompositions having one or more of the following features: wherein the matrix includes PEG and wherein said dye has Formula I:

I

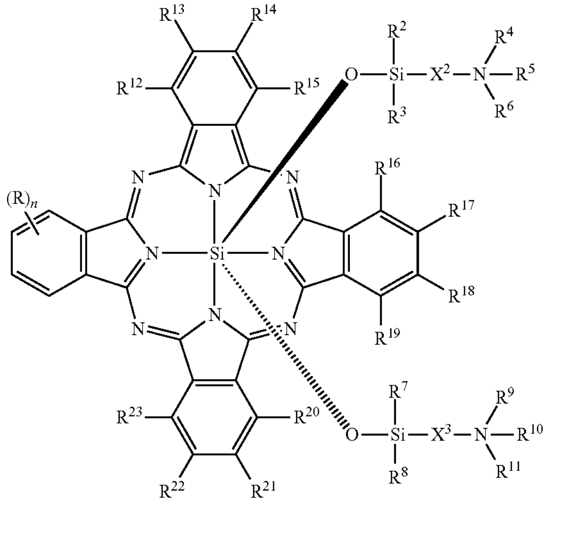

wherein:

R is a member selected from the group consisting of -L-Q and -L-$Z^1$;

L is a member selected from the group consisting of a direct link, or a covalent linkage, wherein said covalent linkage is linear or branched, cyclic or heterocyclic, saturated or unsaturated, having 1-60 atoms selected from the group consisting of C, N, P, O, and S, wherein L can have additional hydrogen atoms to fill valences, and wherein said linkage contains any combination of ether, thioether, amine, ester, carbamate, urea, thiourea, oxy or amide bonds; or single, double, triple or aromatic carbon-carbon bonds; or phosphorus-oxygen, phosphorus-sulfur, nitrogen-nitrogen, nitrogen-oxygen, or nitrogen-platinum bonds; or aromatic or heteroaromatic bonds;

Q is a reactive or an activatable group;

$Z^1$ is a material;

n is 1 or 2;

$R^2$, $R^3$, $R^7$, and $R^8$ are each independently selected from optionally substituted alkyl, and optionally substituted aryl;

$R^4$, $R^5$, $R^6$, $R^9$, $R^{10}$, and $R^{11}$, if present, are each members independently selected from the group consisting of hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ includes a water soluble group;

$R^{12}$, $R^{13}$, $R^{14}$, $R^{15}$, $R^{16}$ $R^{17}$, $R^{18}$, $R^{19}$, $R^{20}$, $R^{21}$, $R^{22}$ and $R^{23}$ are each members independently selected from the group consisting of hydrogen, halogen, optionally substituted alkylthio, optionally substituted alkylamino and optionally substituted alkoxy, or in an alternative embodiment, at least one of i) $R^{13}$, $R^{14}$, and the carbons to which they are attached, or ii) $R^{17}$, $R^{18}$, and the carbons to which they are attached, or iii) $R^{21}$, $R^{22}$ and the carbons to which they are attached, join to form a fused benzene ring; and $X^2$ and $X^3$ are each members independently selected from the group consisting of $C_1$-$C_{10}$ alkylene optionally interrupted by a heteroatom, wherein if n is 1, the phthalocyanine may be substituted either at the 1 or 2 position and if n is 2, each R may be the same or different, or alternatively, they may join to form a 5- or 6-membered ring.

There is further provided these methods, treatments, compositions, kits, and nanocompositions having one or more of the following features: wherein the patient is a human; wherein the animal is a mammal; and, wherein the animal is a human; wherein the animal is a mammal.

DESCRIPTION OF THE PREFERRED EMBODIMENTS

Figure 1:
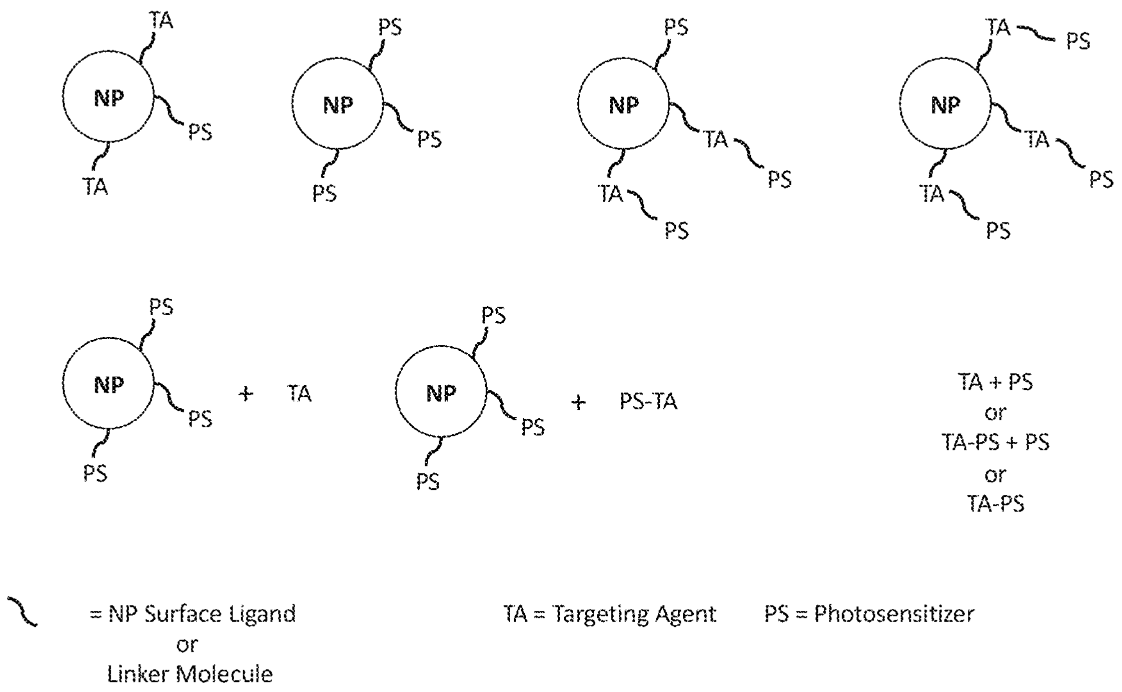
FIG. 1 is a schematic formulaic representation of embodiments of targeted delivery nanocompositions, systems and products, in accordance with the present inventions.

The present inventions relate to nanocompositions having a photosensitizer and a targeting agent, and making, evaluating and using the same. The present inventions relate to nanocompositions having a photosensitizer, and making, evaluating and using the same with a targeting agent. The present inventions relate to nanocompositions, including nanoparticle systems, having targeting agents, for use in photodynamic therapies, diagnostics and theranostics of animal, including mammal and human, conditions and disease. The present inventions relate to nanocompositions for use in photodynamic therapy for a cardiac, oncologic, bariatric, or dermatologic indications, conditions and diseases.

Embodiments of the present inventions relate generally to targeted photodynamic therapies, targeted photosensitizers, including targeted nanoconstructs and uses of these therapies and materials in dynamic therapies for treating, managing, addressing, curing, cardiac, oncologic, bariatric, or dermatologic conditions and diseases in animals including humans.

The present inventions further relate to nanocompositions. In particular, the present inventions provide nanocompositions for clinical (e.g., targeted therapeutic), diagnostic (e.g., imaging), and research applications in the fields of a cardiology, oncology, dermatology, and bariatrics.

An embodiment of the present inventions is a composition having a core molecule, to which a pathogen specific TA and a PS are linked (e.g., chemically, covalently or otherwise attached). In preferred embodiments, the photosensitizer is a phthalocyanine dye, and the core molecule is a multi-arm nanoparticle, a linear molecule, PEG, a multi-arm PEG, 8PEG, 8PEGA and 8PEGMAL. These embodiments is used to provide PDT for cardiac, oncologic, bariatric, or dermatologic conditions and diseases in animals including humans.

The targeting agent (TA) can be an agent e.g., peptide, antibody, protein, or small molecule, that targets a particular cell, cell type, tissue or tissue type (collectively referred to as "target tissue", unless specifically stated otherwise). The TA's, are linked to a nanoparticle to form a nanocomposition that also may have a PS. The TA nanoparticle composition may be used for imaging. The TAs are specific to a particular target tissue, or in embodiments a spices, a group, or a family of pathogens, cells or tissues. The TA can bind to, target or be specific for unique identifiers, e.g., structures, on the target tissue. The TA nanocomposition is transduced into or otherwise affixed to the target tissue at much higher levels than it is transduced into or affixed to other tissues and cells. In certain embodiments the ratio of selectivity of TA nanocomposition for the target tissue relative to all other tissues and cells present in the patient, is at least 2:1 and greater, is at least 3:1 and greater, is at least 4:1 and greater, is at least 10:1 and greater, and is at least 100:1 and greater.

The photoactive agent can be any dye or molecule that produces, or causes the production of, ROS when exposed to light, or produces other compounds when exposed to light that kill, destroy or render inert, the pathogen. Examples of PS include, for example, IR700, methylene blue (MB), chlorin e6 (Ce6), coomassie blue, gold.

An embodiment of the present nanocompositions is a nanoparticle, a phthalocyanine PS, and a TA. This embodiment is used to provide PDT for cardiac, oncologic, bariatric, or dermatologic conditions and diseases in animals including humans.

An embodiment of the present nanocompositions is a nanoparticle, a phthalocyanine PS, where the phthalocyanine is a phthalocyanine die disclosed and taught in U.S. Pat. No. 7,005,518, and a TA. This embodiment is used to provide PDT for cardiac, oncologic, bariatric, or dermatologic conditions and diseases in animals including humans.

An embodiment of the present nanocompositions is a nanoparticle, a phthalocyanine PS, and a TA. This embodiment is used to provide PDT for cardiac, oncologic, bariatric, or dermatologic conditions and diseases in animals including humans.

An embodiment of the present nanocompositions is a nanoparticle, where the nanoparticle is PEG, and preferably 8PEGA, a phthalocyanine PS, and a TA. This embodiment is used to provide PDT for cardiac, oncologic, bariatric, or dermatologic conditions and diseases in animals including humans.

An embodiment of the present nanocompositions is a nanoparticle, where the nanoparticle is PEG, and preferably 8PEGA, a phthalocyanine PS, where the phthalocyanine is a phthalocyanine die disclosed and taught in U.S. Pat. No. 7,005,518, and a TA. This embodiment is used to provide PDT for cardiac, oncologic, bariatric, or dermatologic conditions and diseases in animals including humans.

An embodiment of the present nanocompositions is a nanoparticle, where the nanoparticle is PEG, and preferably 8PEGA, a phthalocyanine PS, where the phthalocyanine is a phthalocyanine die disclosed and taught in U.S. Pat. No. 7,005,518, and a PSTA. This embodiment is used to provide PDT for cardiac, oncologic, bariatric, or dermatologic conditions and diseases in animals including humans.

As used herein 8PEG refers to, and would include, any 8-arm polyethylene glycol (PEG) molecule (e.g., nanoparticle). 8PEG would include all 8PEGs where one or more of the end groups of the arms is modified. For example, 8PEG would include 8PEGA (8PEG-A, and similar terms) which is 8PEG having amine terminated end groups on the arms (one, two and preferably all arms). For example, 8PEG would include 8PEGMAL (8PEG-MAL and similar terms) which is 8PEG having maleimide terminated end groups on the arms (one, two and preferably all arms). These 8PEGs would include nanoparticles having a hydrodynamic diameter (e.g., size) of 25 nm and less, a hydrodynamic diameter of 10 nm and less, and having a hydrodynamic diameter of from about 30 nm to about 5 nm, and having a hydrodynamic diameter of from about 20 nm to about 5 nm. These 8PEGs would include nanoparticles that are 20 kilodaltons (kDa) and greater, that are 40 kDa and greater, and that are from about 15 kDa to about 50 kDa, and that are from about 5 kDa to about 100 kDa.

IRDye 700DX HHS Ester ("IR700") is a preferred photosensitizer for the present embodiments of nanocompositions and for the treatment of pathogen conditions using the present embodiments of the targeted nanoparticle and nanocompositions based photodynamic therapies.

IR700 is a phthalocyanine dye that has minimal sensitive to photobleaching. IR700 is water soluble, having good solubility. It is salt tolerant, having good salt tolerance. IR700 is available from LI-Cor and is an embodiment disclosed in U.S. Pat. No. 7,005,518, the entire disclosure of which is incorporated herein by reference.

IR700 has the following structure:

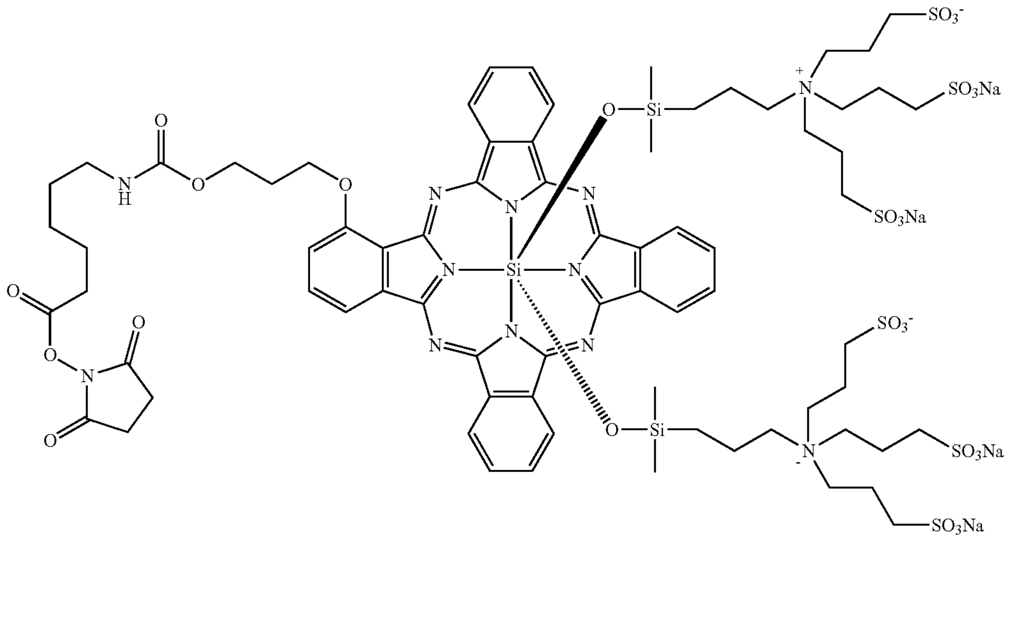

IR700 has the chemical formula $C_{74}H_{96}N_{12}Na_4O_{27}S_6Si_3$

IR700 has a molecular weight of 1954.21 g/mol.

IR700 has an exact mass of 1952.37

IR700 has a maximum absorbance of light at 689 nm. And, also shows much smaller absorbance peaks at 350 nm, and 625 nm.

In embodiments the pathogen targeted nanoparticle with IR700 is activated by delivering, to the target tissue having this nanoparticle, light having a wavelength of from about 550 nm to about 750 nm, light having a wavelength of about 300 to 400, light having wavelengths of about 350 nm about 625 nm and about 689 nm, light from about 600 nm to about 800 nm, light from bout 650 nm to about 725 nm, light from about 675 nm to about 725 nm, light at bout 689 nm, light at 689 nm, and all wavelength within these ranges, as well as higher and lower wavelengths. In an embodiment the light is provided by a laser, and is a laser beam. Preferably, the power of the laser beam, and the amount of energy delivered to the target tissue by the laser beam is below, and well below (e.g., at least 10% below, at least 20% below, at least 50% below) the threshold where the laser beam will heat, damage or cause laser induced optical breakdown. In a preferred embodiment the light that is delivered is eye safe.

For example, in some embodiments, the present nanocompositions provide a method of treating (e.g., ablating) a condition, comprising: a) contacting an animal with a nanoparticle comprising a matrix, a toxic (e.g., ablative) agent (e.g., photosensitizer), and a targeting moiety; and b) administering an activator of the toxic agent (e.g., light) to at least a portion of the target tissue in of the animal to activate the toxic agent. In some embodiments, administering the activator kills (e.g., ablates) the target only where activator is administered and only to target tissue or a specific area where the target tissue may be. In some embodiments, the activator is light. In some embodiments, light from a laser. In some embodiments, the targeting moiety is a targeting peptide. In some embodiments, the photosensitizer is IR700. In some embodiments, the contacting is via intravenous administration. In some embodiments, the nanoparticle is a PEG molecule (e.g., 8-arm PEG). In some embodiments, the nanoparticle is approximately 10 nm or less in size.

In some embodiments, the method further comprises the step of imaging the nanoparticles in the animal. In some embodiments, the imaging is performed after the administering of activator and optionally determines a treatment course of action (e.g., further administering of activator, location of treatment and/or nanoparticles). In further embodiments, the present invention provides compositions and kits comprising the aforementioned nanoparticles and any additional components necessary, sufficient or useful in addressing cardiac, oncologic, bariatric, or dermatologic conditions and diseases in animals including humans.

In yet other embodiments, the present invention provides the use of the aforementioned nanoparticles (e.g., in tissue ablation). In still further embodiments, the present invention provides systems comprising a) the aforementioned nanoparticles; and b) an instrument for delivery of activator (e.g., a laser or ultrasound instrument). In some embodiments, systems further comprise imaging components (e.g., to image or bound to nanoparticles in pathogens) and computer software and computer processor for controlling the system. In some embodiments, the computer software and computer processor are configured to control the delivery of the activator, image the nanoparticle, and displaying an image of the nanoparticle.

US Patent Publication No. 2015/0328315 teaches and disclose photodynamic therapies, nanocompositions, targeted nanocompositions, imaging and theranostics, the entire disclosure of which is incorporated herein by reference.

The photosensitizer (PS) can be any dye or molecule that produces ROS when exposed to light, or produces other compounds when exposed to light that kill the pathogen. Examples of photoactive agents include, for example, methylene blue (MB), chlorin e6 (Ce6), coomassie blue, gold.

The PS can be the compositions disclosed and taught in U.S. Pat. Nos. 8,562,944, 8,906,343, and 9,045,488.

The PS can be PHOTOFRIN,

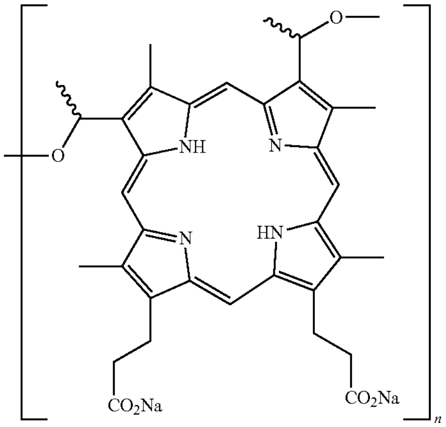

Photofrin (n = 1-9)

The PS can be Photochlor (CAS #149402-51-7)

The PS can be

| PHOTOSENSITIZER | STRUCTURE | WAVELENGTH, nm |
|---|---|---|
| Porfimer sodium (Photofrin) (BPD) | Porphyrin | 630 |
| ALA | Porphyrin precursor | 635 |
| ALA esters | Porphyrin precursor | 635 |
| Temoporfin (Foscan) (mTHPC) | Chlorine | 652 |
| Verteporfin | Chlorine | 630 |
| HPPH | Chlorin | 665 |
| SnEt2 (Purlytin) | Chlorin | 660 |
| Talaporfin (LS11, MACE, NPs6) | Chlorin | 660 |
| Ce6-PVP (Fotolon, Ce6 derivitives (Radachlorin, Photodithazi) | Chlorin | 660 |
| Silicon phthalocyanine (Pc4) | Phthalocyanine | 675 |
| Padoporfin (TOOKAD) | Bacteriochlorin | 762 |
| Motexafin lutetium (Lutex) | Texaphyrin | 732 |

Embodiments of the present nanocompositions, including 8PEG-CPT nanocompositions, have a PS that is a dye having the following formula of Formula I:

I

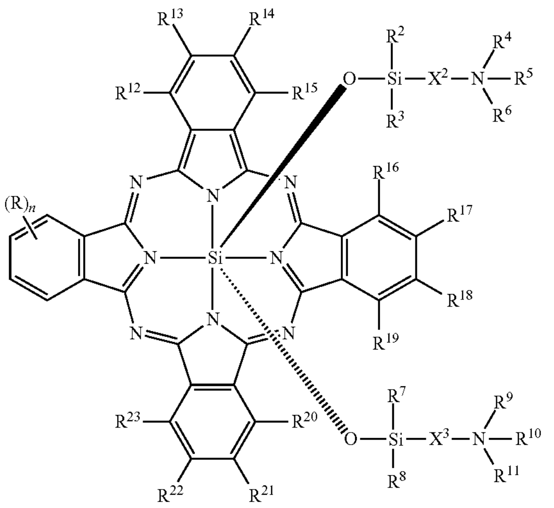

wherein: R is a member selected from the group consisting of -L-Q and -L-$Z^1$; L is a member selected from the group consisting of a direct link, or a covalent linkage, wherein said covalent linkage is linear or branched, cyclic or heterocyclic, saturated or unsaturated, having 1-60 atoms selected from the group consisting of C, N, P, O, and S, wherein L can have additional hydrogen atoms to fill valences, and wherein said linkage contains any combination of ether, thioether, amine, ester, carbamate, urea, thiourea, oxy or amide bonds; or single, double, triple or aromatic carbon-carbon bonds; or phosphorus-oxygen, phosphorus-sulfur, nitrogen-nitrogen, nitrogen-oxygen, or nitrogen-platinum bonds; or aromatic or heteroaromatic bonds; Q is a reactive or an activatable group; $Z^1$ is a material; n is 1 or 2; $R^2$, $R^3$, $R^7$, and $R^8$ are each independently selected from optionally substituted alkyl, and optionally substituted aryl; $R^4$, $R^5$, $R^6$, $R^9$, $R^{10}$, and $R^{11}$, if present, are each members independently selected from the group consisting of hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group; $R^{12}$, $R^{13}$, $R^{14}$, $R^{15}$, $R^{16}$ $R^{17}$, $R^{18}$ $R^{19}$, $R^{20}$, $R^{21}$, $R^{22}$ and $R^{23}$ are each members independently selected from the group consisting of hydrogen, halogen, optionally substituted alkylthio, optionally substituted alkylamino and optionally substituted alkoxy, or in an alternative embodiment, at least one of i) $R^{13}$, $R^{14}$, and the carbons to which they are attached, or ii) $R^{17}$, $R^{18}$, and the carbons to which they are attached, or iii) $R^{21}$, $R^{22}$ and the carbons to which they are attached, join to form a fused benzene ring; and $X^2$ and $X^3$ are each members independently selected from the group consisting of $C_1$-$C_{10}$ alkylene optionally interrupted by a heteroatom, wherein if n is 1, the phthalocyanine may be substituted either at the 1 or 2 position and if n is 2, each R may be the same or different, or alternatively, they may join to form a 5- or 6-membered ring.

Embodiments of the present nanocompositions, including 8PEGA-CPT nanocompositions have a PS that is a dye having the following formula of Formula Ia:

Ia

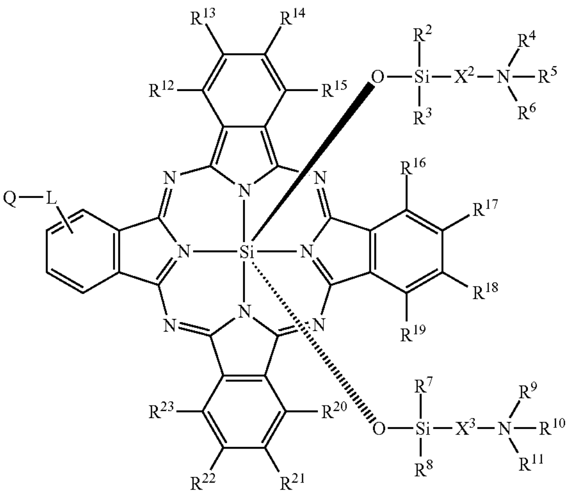

wherein: $R^2$, $R^3$, $R^7$, and $R^8$ are each independently selected from optionally substituted alkyl, and optionally substituted aryl; $R^4$, $R^5$, $R^6$, $R^9$, $R^{10}$, and $R^{11}$, if present, are each members independently selected from the group consisting of hydrogen, optionally substituted alkyl, optionally substituted alkanoyl, optionally substituted alkoxycarbonyl, optionally substituted alkylcarbamoyl, wherein at least one of $R^4$, $R^5$, $R^6$, $R^9$, $R^{10}$, and $R^{11}$ comprises a water soluble group; and $R^{12}$, $R^{13}$, $R^{14}$, $R^{15}$, $R^{16}$ $R^{17}$, $R^{18}$, $R^{19}$, $R^{20}$, $R^{21}$, $R^{22}$ and $R^{23}$ are each members independently selected from the group consisting of hydrogen, halogen, optionally substituted alkylthio, optionally substituted alkylamino and optionally substituted alkoxy, or in an alternative embodiment, at least one of i) $R^{13}$, $R^{14}$, and the carbons to which they are attached, or ii) $R^{17}$, $R^{18}$, and the carbons to which they are attached, or iii) $R^{21}$, $R^{22}$ and the carbons to which they are attached, join to form a fused benzene ring.

In embodiments L has the following formula $$—R^1—Y—X^1—Y^1—$$

wherein $R^1$ is a bivalent radical or a direct link; Y and $Y^1$ are each independently selected from the group consisting of a direct link, oxygen, an optionally substituted nitrogen and sulfur; and $X^1$ is a member selected from the group consisting of a direct link and $C_1$-$C_{10}$ alkylene optionally interrupted by a heteroatom.

In further embodiments, $R^1$ is a bivalent radical selected from the group consisting of optionally substituted alkylene, optionally substituted alkyleneoxycarbonyl, optionally substituted alkylenecarbamoyl, optionally substituted alkylenesulfonyl, optionally substituted alkylenesulfonylcarbamoyl, optionally substituted arylene, optionally substituted arylenesulfonyl, optionally substituted aryleneoxycarbonyl, optionally substituted arylenecarbamoyl, optionally substituted arylenesulfonylcarbamoyl, optionally substituted carboxyalkyl, optionally substituted carbamoyl, optionally substituted carbonyl, optionally substituted heteroarylene, optionally substituted heteroaryleneoxycarbonyl, optionally substituted heteroarylenecarbamoyl, optionally substituted heteroarylenesulfonylcarbamoyl, optionally substituted sulfonylcarbamoyl, optionally substituted thiocarbonyl, a optionally substituted sulfonyl, and optionally substituted sulfinyl.

In further embodiments, $R^1$ is $R^2$, $R^3$, $R^7$, and $R^8$ are each independently selected from optionally substituted alkyl, and optionally substituted aryl, $R^4$, $R^5$, $R^6$, $R^9$, $R^{10}$, and $R^{11}$, if present, are each members independently selected from an optionally substituted alkyl, wherein at least two members of the group consisting of $R^4$, $R^5$, $R^6$, $R^7$, $R^8$, and $R^9$ comprise a water soluble functional group; $R^{12}$, $R^{13}$, $R^{14}$, $R^{15}$, $R^{16}$ $R^{17}$, $R^{18}$, $R^{19}$, $R^{20}$, $R^{21}$, $R^{22}$ and $R^{23}$ are each hydrogen, halogen, optionally substituted alkylthio, optionally substituted alkylamino and optionally substituted alkoxy, or in an alternative embodiment, at least one of $R^{13}$, $R^{14}$, and the carbons to which they are attached, or $R^{17}$, $R^{18}$, and the carbons to which they are attached, or $R^{21}$, $R^{22}$ and the carbons to which they are attached, join to form a fused benzene ring; $X^1$, $X^2$ and $X^3$ are each members independently selected from the group consisting of $C_1$-$C_{10}$ alkylene optionally interrupted by a heteroatom; and Y and $Y^1$ are each independently selected from the group consisting of a direct link, oxygen, an optionally substituted nitrogen and sulfur.

In further embodiments, $R^2$, $R^3$, $R^7$, and $R^8$ are each independently selected from optionally substituted methyl, ethyl, and isopropyl; $R^4$, $R^5$, $R^6$, $R^9$, $R^{10}$, and $R^{11}$, if present, are each members independently selected from an optionally substituted alkyl, wherein at least two members of the group consisting of $R^4$, $R^5$, $R^6$, $R^7$, $R^8$, and $R^9$ comprise a substituent selected from the group consisting of a carboxylate ($-CO_2^-$) group, a sulfonate ($-SO_3^-$) group, a sulfonyl ($-SO_2^-$) group, a sulfate ($-SO_4^{-2}$) group, a hydroxyl (—OH) group, a phosphate ($-OPO_3^{-2}$) group, a phosphonate ($-PO_3^{-2}$) group, an amine ($-NH_2$) group and an optionally substituted quaternized nitrogen with each having an optional counter ion; $R^{12}$, $R^{13}$, $R^{14}$, $R^{15}$, $R^{16}$ $R^{17}$, $R^{18}$, $R^{19}$, $R^{20}$, $R^{21}$, $R^{22}$ and $R^{23}$ are each hydrogen; $X^1$, $X^2$ and $X^3$ are each members independently selected from the group consisting of $C_1$-$C_{10}$ alkylene optionally interrupted by a heteroatom; and Y and $Y^1$ are each independently selected from the group consisting of a direct link, oxygen, an optionally substituted nitrogen and sulfur.

Embodiments of the present nanocompositions, including 8PEGA-CPT nanocompositions have a PS that is a dye having the following formula:

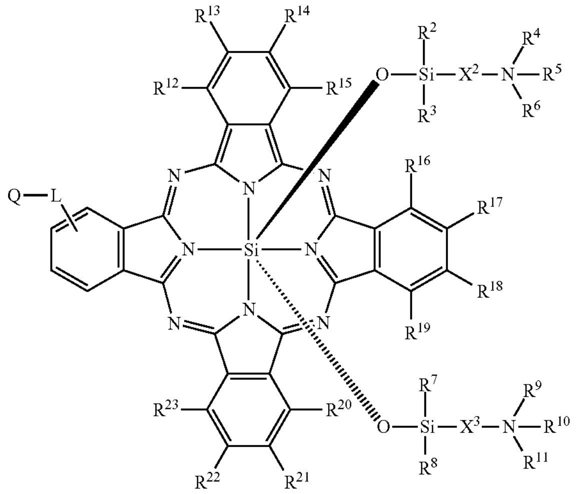

wherein Q is a reactive or an activatable group selected from the group consisting of an alcohol, an activated ester, an acyl halide, an alkyl halide, an optionally substituted amine, an anhydride, a carboxylic acid, a carbodiimide, hydroxyl, iodoacetamide, an isocyanate, an isothiocyanate, a maleimide, an NHS ester, a phosphoramidite, a platinum complex, a sulfonate ester, a thiol, and a thiocyanate.

Embodiments of the present nanocompositions, including 8PEGA-CPT nanocompositions have a PS that is a dye having the following formula of Formula 1b:

Ib

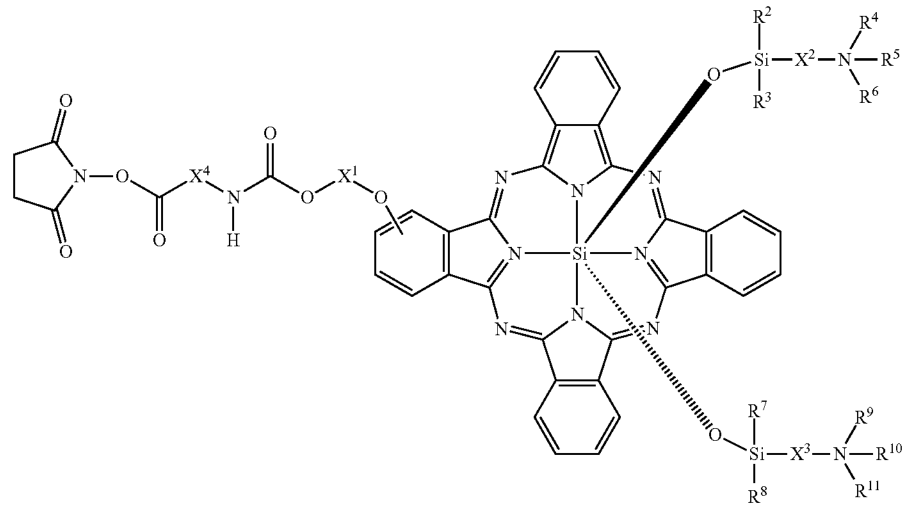

wherein $X^4$ is a $C_1$-$C_{10}$ alkylene optionally interrupted by a heteroatom.

Embodiments of the present nanocompositions, including 8PEGA-CPT nanocompositions have a PS that is a dye having the formula of Formula 1c:
Ic
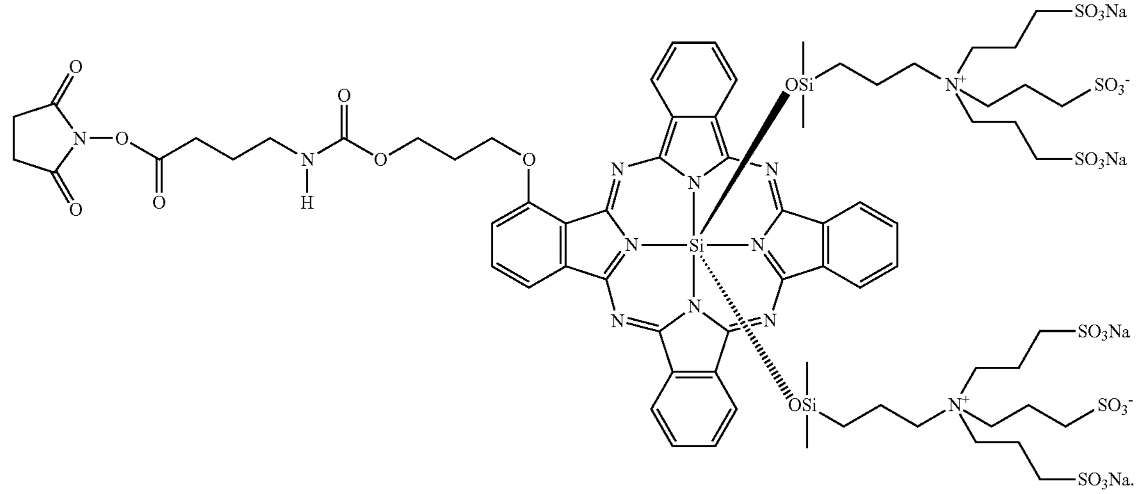
Embodiments of the present nanocompositions, including 8PEGA-CPT nanocompositions have a PS that is a dye having the following formula of Formula 1d:
Id
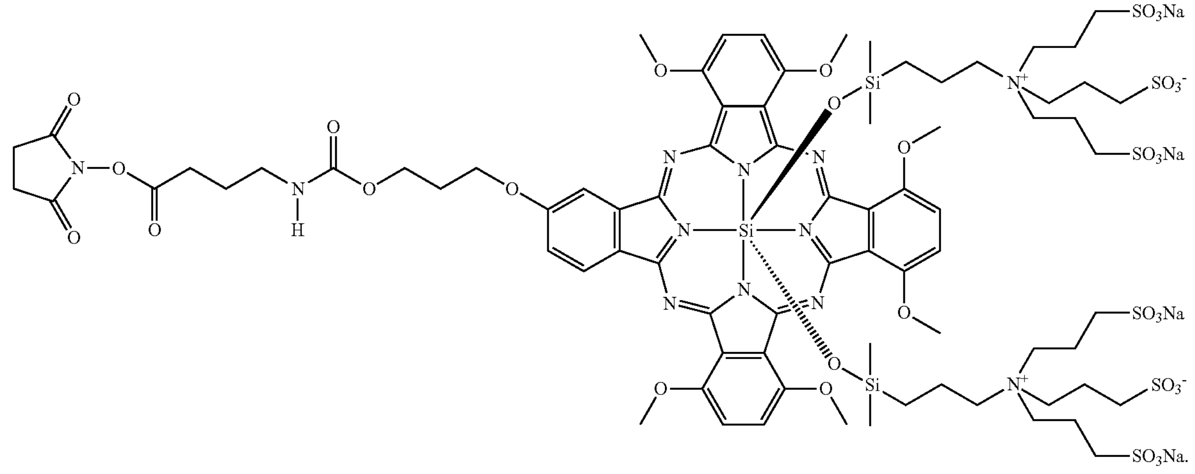

Embodiments of the present nanocompositions, including 8PEGA-CPT nanocompositions have a PS that is a dye having the following formula of Formula 1d-1:
Id-1
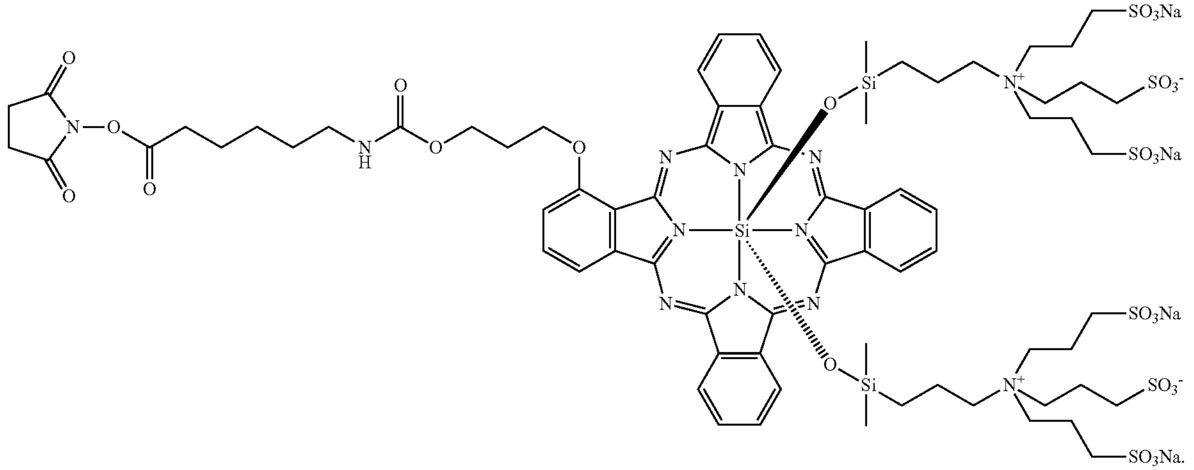
Embodiments of the present nanocompositions, including 8PEGA-CPT nanocompositions have a PS that is a dye having the following formula of Formula 1e:
Ie
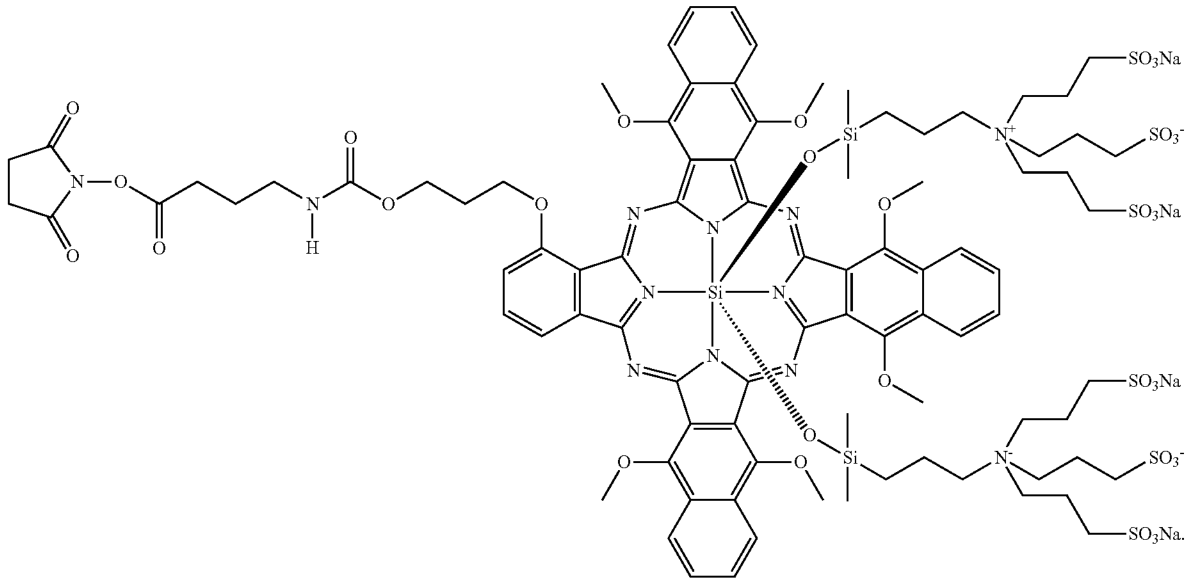

Embodiments of the present nanocompositions, including 8PEGA-CPT nanocompositions have a PS that is a dye having the following formula of Formula 1e-1:
Ie-1
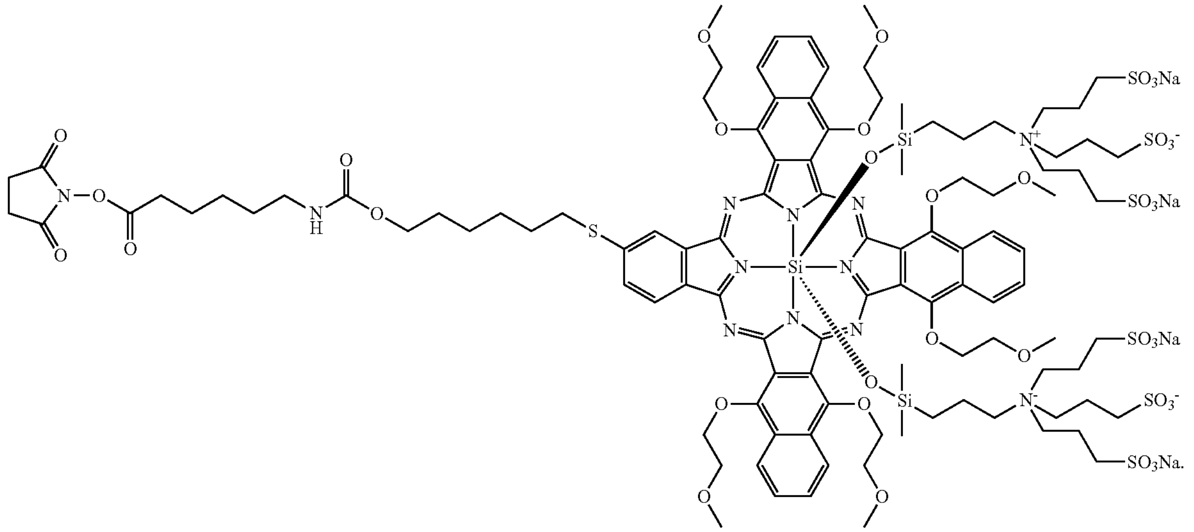
Embodiments of the present nanocompositions, including 8PEGA-CPT nanocompositions have a PS that is a dye having the following formula:
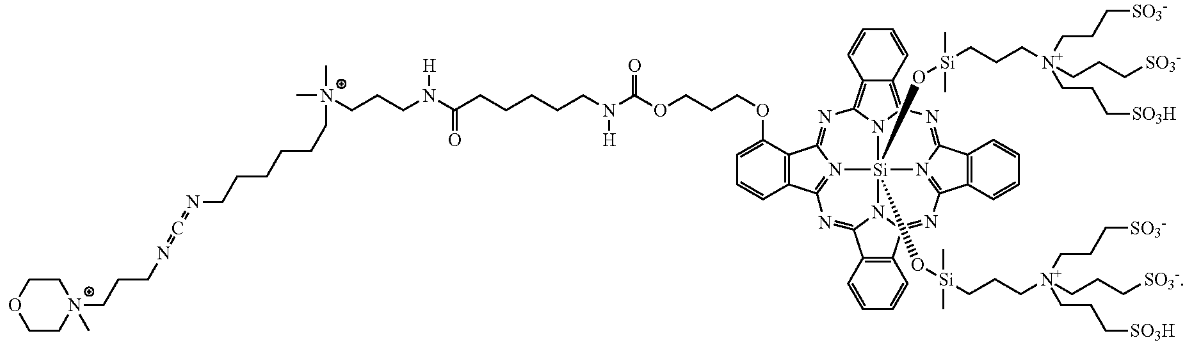

Embodiments of the present nanocompositions, including 8PEGA-CPT nanocompositions have a PS that is a dye having the following formula:

If

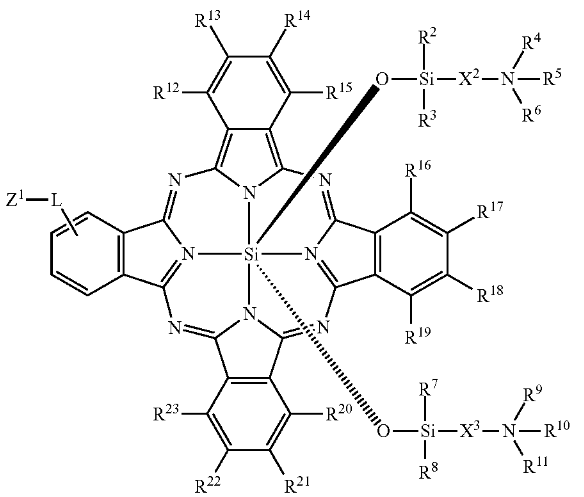

wherein: $Z^1$ is the nanoparticle; L is a member selected from the group consisting of a direct link, or a covalent linkage, wherein said covalent linkage is linear or branched, cyclic or heterocyclic, saturated or unsaturated, having 1-60 atoms selected from the group consisting of C, N, P, O, and S, wherein L can have additional hydrogen atoms to fill valences, wherein said linkage contains any combination of ether, thiether, amine, ester, carbamate, urea, thiourea, oxy or amide bonds; or single, double, triple or aromatic carbon-carbon bonds; or phosphorus-oxygen, phosphorus-sulfur, nitrogen-nitrogen, nitrogen-oxygen, or nitrogen-platinum bonds; or aromatic or heteroaromatic bonds; $R^2$, $R^3$, $R^7$, and $R^8$ are each independently selected from optionally substituted alkyl, and optionally substituted aryl; $R^4$, $R^5$, $R^6$, $R^9$, $R^{10}$, and $R^{11}$, if present, are each members independently selected from the group consisting of hydrogen, optionally substituted alkyl, optionally substituted alkanoyl, optionally substituted alkoxycarbonyl, optionally substituted alkylcarbamoyl, and a chelating ligand, wherein at least one of $R^4$, $R^5$, $R^6$, $R^9$, $R^{10}$, and $R^{11}$ comprises a water soluble group; $R^{12}$, $R^{13}$, $R^{14}$, $R^{15}$, $R^{16}$ $R^{17}$, $R^{18}$, $R^{19}$, $R^{20}$, $R^{21}$, $R^{22}$ and $R^{23}$ are each members independently selected from the group consisting of hydrogen, halogen, optionally substituted alkylthio, optionally substituted alkylamino and optionally substituted alkoxy, or in an alternative embodiment, at least one of i) $R^{13}$, $R^{14}$, and the carbons to which they are attached, or ii) $R^{17}$, $R^{18}$, and the carbons to which they are attached, or iii) $R^{21}$, $R^{22}$ and the carbons to which they are attached, join to form a fused benzene ring; and $X^2$ and $X^3$ are each members independently selected from the group consisting of $C_1$-$C_1$ alkylene optionally interrupted by a heteroatom.

In general, and typically, PSs do not have any general affinity for specific tissues, other than certain classes generally favoring rapidly dividing cells (e.g. chlorins in cancer). Thus, in embodiments a targeted delivery of PDT, is beneficial, and in situations necessary to achieve a high contrast ratio between the target tissue, e.g., the tissue to be ablated and bystander tissues, e.g., the tissue that is intended to be unaffected by, and not damaged by, the PDT.

Targeted delivery of a PS may take several different forms: conjugation of a PS to a nanoparticle (NP), conjugation of a PS to a targeting agent (TA), conjugation of both a PS and TA to a NP (the PS being on the NP, the TA, or both), co-administration of a PS (with or without a NP) with a TA, or any combination thereof. Examples of some of these configurations for the present nanocompositions is shown in FIG. 1.

TAs include, for example, a small molecule, a protein, a peptide, an enzyme substrate, a hormone, an antibody, an antigen, a hapten, an avidin, a streptavidin, biotin, a carbohydrate, an oligosaccharide, a polysaccharide, a nucleic acid, a deoxy nucleic acid, a fragment of DNA, a fragment of RNA, nucleotide triphosphates, acyclo terminator triphosphates, peptide nucleic acid (PNA) biomolecules, and combinations and variations of these.

Figure 2:
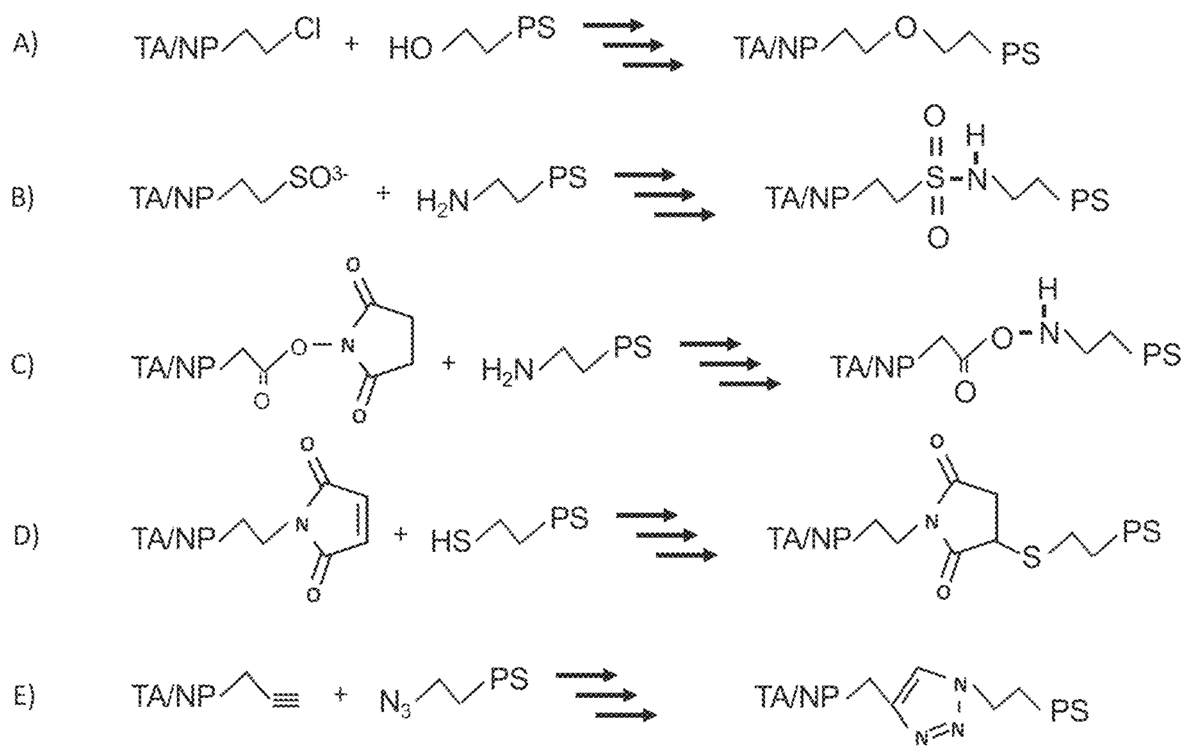
FIG. 2 is a schematic formulaic representation of embodiments of various NP, TA and PS parings and combinations in accordance with the present inventions.

Turning to FIG. 2 there is shown embodiments of methods by which a PS may be covalently conjugated to a TA or NP. These methods are useful and applicable across most combinations, and so they are generally discussed as if they are a single method. Thus, any given method of NP conjugation should also be viable for TA conjugation. It further being understood that as a general requirement the functional groups employed should match each other. Tables 2-4 show a list of pairings and the resulting bonds formed between a TA, NP, or PS for examples of embodiments of combinations for embodiments of the present nanocompositions.

Figure 3:
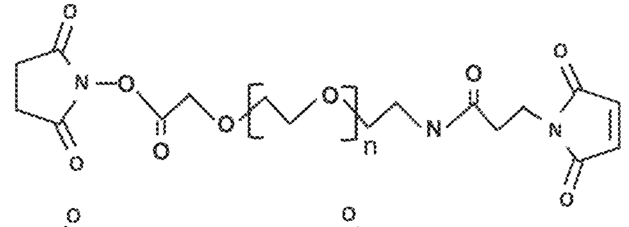
FIG. 3 is a formulaic representation of embodiments of linkers and functional group conversions in accordance with the present inventions.
Figure 3:
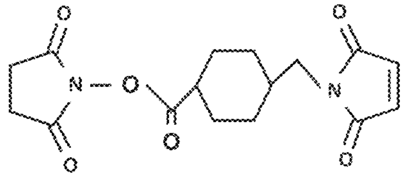
Figure 3:
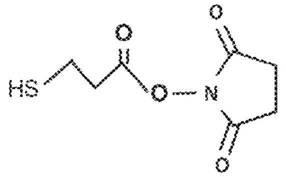
Figure 3:
Figure 3:
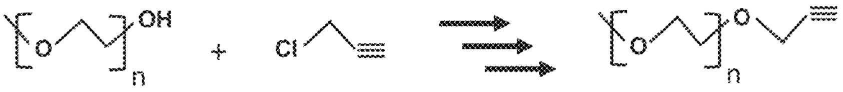

Optionally, conjugation of the PS to a TA, NP, or both, may include a spacer or linker molecule or group. Typically, this will not change the chemistry employed, but it can be used to convert functional groups from one set to another (e.g., an alcohol may be converted to an alkyne with a linking group to enable a different reaction protocol). The linkers may originate on the PS, TA, NP, or any combination, and may be a small molecule chain or polymer. FIG. 3 shows some example linkers and an end group conversion.

An embodiment of a final product would be a NP of small hydrodynamic diameter, preferably from a family of linear, branched, or cyclic macropolymers. Proteins, may also be used as they can be small enough, however, they may have competing pharma co-kinetic behavior with the TA. Examples of macropolymers for the NP would include: polyethylene glycol (PEG), poly amidoamine (PAMAM), polyethyleneimine (PEI), polyvinyl alcohol, and poly L-lysine. The preferred platform is PEG, specifically 8-arm branched PEG (8PEG), because of its widely known non-toxicity.

The various embodiments of the nanocompositions disclosed and taught herein can use or have multi-arm PEG NPs, this would include 8PEG and other numbers of arms, including 4-arm PEG, including 4PEGA (amine terminated end groups on the arms (one, two and preferably all arms)) and 4PEGMAL (having maleimide terminated end groups on the arms (one, two and preferably all arms)) and 6-arm PEG (including 6PEGA (amine terminated end groups on the arms (one, two and preferably all arms)) and 6PEGMAL (having maleimide terminated end groups on the arms (one, two and preferably all arms)).

Figure 4:
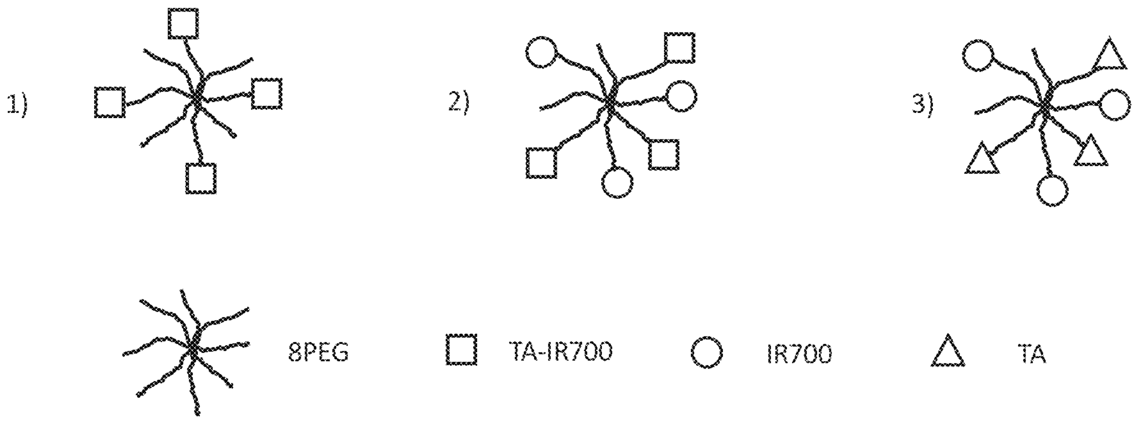
FIG. 4 is a schematic formulaic representation of a nanocomposition in accordance with the present inventions.

In an embodiment PEG, in particular 8PEG, conjugation can include both a TA and IR700 and may take, for example, the 3 Forms as shown in FIG. 4.

FIG. 4, Form 1) has a TA-IR700 conjugate that is attached to 8PEGA to provide a TA-PS-NP nanocomposition, having four IR700-TA conjugates attached to the 8PEGA.

FIG. 4, Form 2) is a TA-NP-TA-PS nanocomposition. Form 2) has three TA-IR700 conjugates attached to the 8PEGA, and has three IR700 dye molecules attached to the 8PEGA.

FIG. 4, Form 3) is a TA-NP-PA nanocomposition. Form 3) has three IR700 dye molecules attached to the 8PEGA, and has three TAs attached to the 8PEGA.

These forms do not have TAs and PSs bonded to every arm of the 8PEGA. Thus, Form 1) has three unbonded, or open, or non-active arms. Forms 2) and 3) have two unbonded, or open, or non-active arms. The unbonded arms, typically have end or terminus groups that are, for example, cysteine.

Additionally, the order of conjugation of a TA or IR700 to 8PEG is generally interchangeable for Forms 2) and 3); in this manner the IR700s can be attached first and then the TAs, or the TAs first and then the IR700s. A preferred embodiment would be Form 3), with the order of attachment being, attaching IR700s to 8PEG first, and then attaching the TAs to the 8PEGA. A benefit of this preferred method, among others, is to permit all 8PEGs to have at least one IR700 attached without risking the functionality of the TA by further modifying it.

Contrary to the general teaching of the art, it has been discovered that increasing the number of PS attached to the NP does not necessarily increase the amount of ROS produced, and does not necessarily increase the efficacy of the nanocomposition. Thus, for situations having four or more PS attached to an NP, and in particular 8PEGA, the ROS production and the efficacy of the nanocomposition may be decreased when compared to a nanocomposition having three or less PS. It is theorized that this occurs because of several facts relating to the spacing of the PS, and thus their ability to produce ROS from the in situ oxygen.

Thus, embodiments of IR700-8PEGA-TA nanocompositions have from 1-2 IR700 dyes per 8PEGA, and 3-5 TAs per 8PGEA. These and other embodiments can have a ratio of TA to IR700 that is 2.5 to 1 and greater, 3 to 1 and greater, and 5 to 1 and greater. These and other embodiments can have 1, 2, 3, and 4 free arms and more. It being understood that embodiments having lower rations of TA to IR700 per 8PEGA may also be utilized, including rations of 2 to 1 and 1 to 1. All combinations and variations of these configurations are also contemplated.

Thus, and generally, embodiments of PS-NP-TA nanocompositions have from 1-2 PS per 8PEGA, and 3-5 TA per 8PGEA. Embodiments of these, and other, nanocompositions have a ratio of TA to PS per NP that is 2.5 to 1 and greater, 3 to 1 and greater, and 5 to 1 and greater. These and other embodiments can have 1, 2, 3, and 4 free arms and more. It being understood that embodiments having lower rations of TA to PS per NP may also be utilized, including rations of 2 to 1 and 1 to 1. All combinations and variations of these configurations are also contemplated.

Figure 5A:
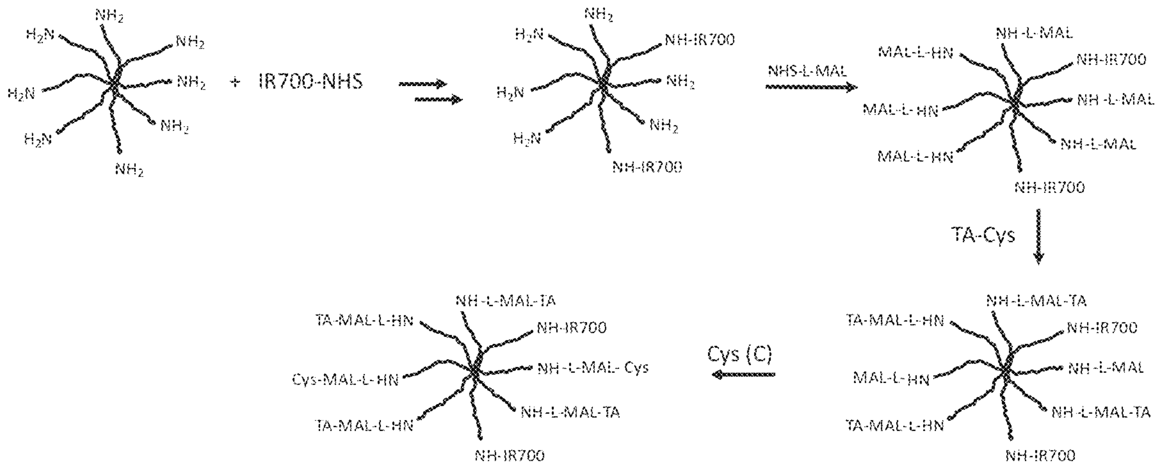
FIG. 5A is a flow diagram of an embodiment of a process for making an embodiment of a nanocomposition in accordance with the present inventions.

Turning to FIG. 5A there is provided an embodiment of a method to produce the nanocomposition of FIG. 4, Form 3). FIG. 5A has the following steps:

IR700-NHS is added to 8PEG-Amine (8PEGA)

A linker (L) is added to 8PEGA to convert the amines to maleimides (MAL)

IR700-8PEGM is treated with thiol terminated (preferably cysteine, cys) TA

Additional free cysteine is added to cap unreacted MAL groups

Figure 5B:
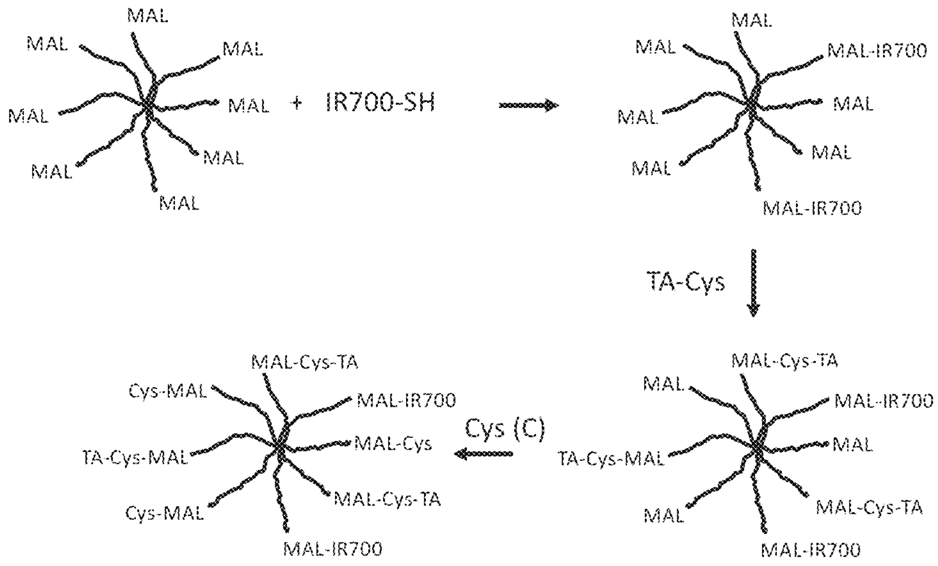
FIG. 5B is a flow diagram of an embodiment of a process for making an embodiment of a nanocomposition in accordance with the present inventions.

Turning to FIG. 5B there is provided an embodiment of a method to produce the nanocomposition of FIG. 4, Form 3). FIG. 5B has the following steps:

IR700-SH is added to 8PEGMAL

IR700-8PEGMAL is treated with thiol terminated TA (preferably cysteine, cys)

Additional free cysteine is added to cap unreacted MAL groups

Figure 6A:
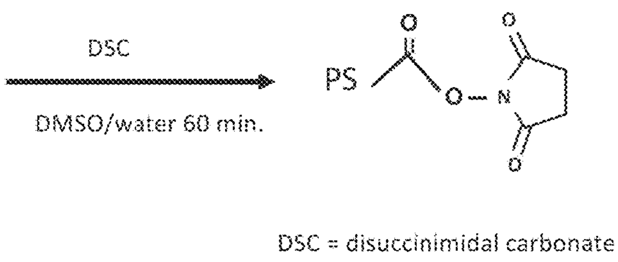
FIG. 6A is a flow diagram of an embodiment of a process for making an embodiment of a PS for use in making a nanocomposition in accordance with the present inventions.
Figure 6B:
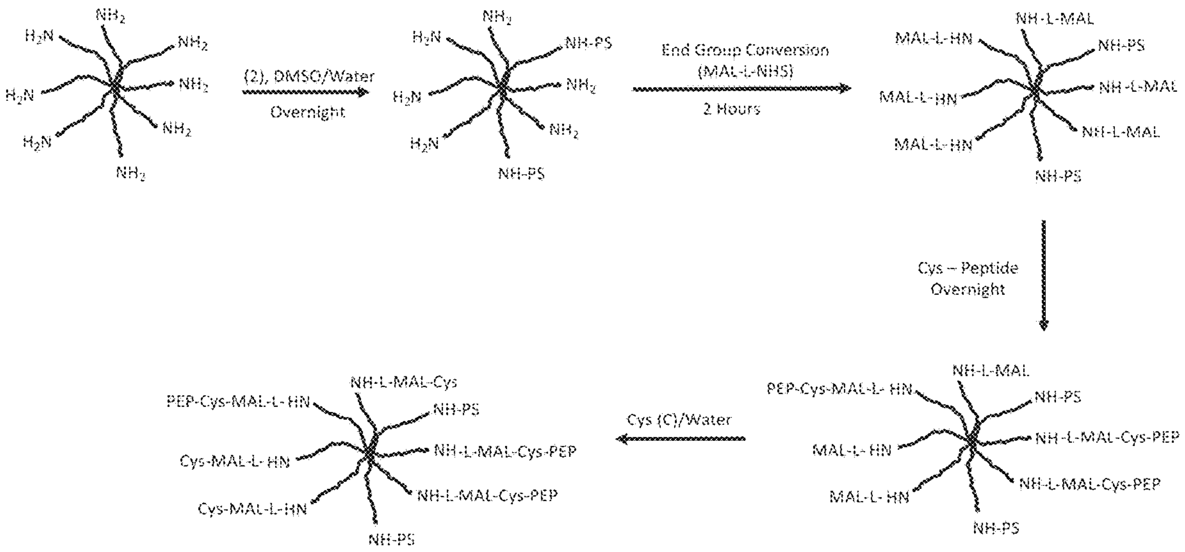
FIG. 6B is a flow diagram of an embodiment of a process for making an embodiment of a nanocomposition in accordance with the present inventions.

Turning to FIGS. 6A and 6B there is shown a general process for forming targeted nanocompositions for PDT, including an IR700-NP-TA nanocomposition. "PEP", (a peptide), is the TA. The end group conversions step of FIG. 6B uses a chemical such as SMCC, BiPEG, or others, that converts the 8PEGA amines to maleimides ("MAL").

FIG. 6A shows the preparation of the NHS ester (SCM, i.e., succinimidyl ester) for the PS, IR700 (formula (2)). FIG. 6B shows the preparation of the nanocomposition using the HHS ester (FIG. 6A, formula (2)) and a PEP TA.

Covalent conjugation of a NP-X, PS-L-Q, or TA-Z in any combination may take many forms; generally the entities should have X, Q, and Z functional groups that are reactive towards each other. X, Q, and Z include, but are not limited to: alkyl halides, acyl halides, aromatic phenyls, aromatic halides (preferably iodo), carboxylic acids, sulfonic acids, phosphoric acids, alcohols (preferably primary), maleimides, esters, thiols, azides, aldehydes, alkenes (mono or diene), isocyanates, isothiocyanates, amines, anhydrides, or thiols. Tables 2-4 show the matching relevant combinations of NP-X, PS-L-Q, and TA-Z functional groups for conjugation.

TABLE 2

X and Q pairings of NP-X and PS-L-Q for covalent conjugation [Makes PS(L)-NP-X]

| NP-X | PS-L-Q | Conditions | Covalent Bond |
|---|---|---|---|
| Alkyl Halide (Chlorine) | PS-OH | Base, $CHCl_3$ or DMSO | Ether |
| | PS-SH | | Thio Ether |
| | PS-COOH | | Ester |
| | PS-$NH_2$ | | |
| Acyl Halide (Chlorine) | PS-$NH_2$ | 1.5:1 Base:PS-Y (Opt) $CHCl_3$ or DMSO | Amide |
| | PS-SH | | Thio Ester |
| | PS-OH | | Ester |
| | PS-Phenyl | | Ketone |
| Aromatic (Phenyl) | PS-Cl | $AlCl_3$, $CHCl_3$ or DMSO | Alkyl chain |
| | PS-COCl | | ketone |
| Aromatic (Halide Phenyl) | PS-$NH_2$ | Base, $CHCl_3$ or DMSO | Secondary Amine |
| | PS-OH | | Ether |
| | PS-SH | | Thioether |
| Carboxylic Acid | PS-OH | Acid, $CHCl_3$ or DMSO; | Ester |
| | PS-$NH_2$ | | Amide |

TABLE 2-continued

X and Q pairings of NP-X and PS-L-Q for covalent conjugation [Makes PS(L)-NP-X]

| NP-X | PS-L-Q | Conditions | Covalent Bond |
|---|---|---|---|
| | PS-Cl<br>PS-SH | Acid, $CHCl_3$ or DMSO;<br>Base, $CHCl_3$ or DMSO;<br>Acid, $CHCl_3$ or DMSO | Ester<br>Thioester |
| Sulfonic Acid | PS-OH<br>PS-$NH_2$<br>PS-SH | 1.5:1 Base:PS-Y<br>$PCl_5$, $CHCl_3$ or DMSO;<br>$SOCl_2$ may also be used | Sulfonic ester<br>Amino Sulfonate<br>Sulfonic thioester |
| Phosphoric Acid | PS-OH<br>PS-$NH_2$<br>PS-SH | 1.5:1 Base:PS-Y<br>$SOCl_2$, $CHCl_3$ or DMSO | Phosphoramidite |
| Alcohol (Primary) | PS-Cl<br>PS-COOH<br>PS-ester<br>PS-thioester<br>PS-anhydride<br>PS-CHO<br>PS-ITC<br>PS-IC | Base, $CHCl_3$ or DMSO;<br>Base, $CHCl_3$ or DMSO;<br>Base, $CHCl_3$ or DMSO;<br>Base, $CHCl_3$ or DMSO;<br>Base, Pd catalyst, $CHCl_3$;<br>1.5:1 Base:PS-Y, $CHCl_3$;<br>1.5:1 Base:PS-Y, $CHCl_3$ | Ether<br>Ester<br>Ester<br>Ester<br>Ester<br>Ester<br>Thiocarbamate<br>Urethane |
| Maleimide (MAL) | PS-SH | pH 6-8 in water;<br>1.5:1 Base:PS-Y in organic solvent | Thioether |
| Ester | PS-$NH_2$<br>PS-OH<br>PS-SH | Acid, $CHCl_3$ or DMSO | Amide<br>Ester<br>Thioester |
| Thiol | PS-Mal<br>PS-ITC<br>PS-IC | pH 6-8 in water;<br>1.5:1 Base:PS-Y, $CHCl_3$;<br>1.5:1 Base:PS-Y, CHCh | Thioether<br>Dithiocarbamate<br>Thiourethane |
| Azide | PS-Alkyne | Cu(I), $CHCl_3$ or DMSO;<br>Cu free, $CHCl_3$ or water | Triazole |
| Aldehyde | PS-NH2<br>PS-OH | CuI, TBHP, CHCl3;<br>Base, Pd catalyst, $CHCl_3$; | Amide<br>Ester |
| Alkene | PS-Diene | Diels-Alder | Cyclo-alkyl |
| Alkyne | PS-Azide | Cu(I), $CHCl_3$ or DMSO;<br>Cu free, $CHCl_3$ or water | Triazole |
| isocyanate | PS-OH<br>PS-$NH_2$<br>PS-SH | Base, $CHCl_3$;<br>$CHCl_3$;<br>Base, $CHCl_3$ | Urethane<br>Urea<br>Thiourethane |
| isothiocyanate | PS-SH<br>PS-$NH_2$<br>PS-OH | 1.5:1 Base:PS-Y, $CHCl_3$;<br>pH 7.4 in water;<br>1.5:1 Base:PS-Y, $CHCl_3$ | Dithiocarbamate<br>Thiourea<br>Thiocarbamate |
| Amine (A) | PS-COOH<br>PS-COCl<br>PS-NHS<br>PS-CHO<br>PS-ITC<br>PS-IC | Acid, $CHCl_3$ or DMSO;<br>Base (Opt), $CHCl_3$<br>pH 7.4 in water;<br>Base, Pd catalyst, $CHCl_3$;<br>pH 7.4 in water;<br>pH 7.4 in water | Amide<br>Amide<br>Amide<br>Amide<br>Thiourea<br>Urea |

TABLE 2-continued

X and Q pairings of NP-X and PS-L-Q for covalent conjugation [Makes PS(L)-NP-X]

| NP-X | PS-L-Q | Conditions | Covalent Bond |
|---|---|---|---|
| Anhydride | $PS-NH_2$<br>PS-OH<br>PS-SH | CHCl3 or DMSO;<br>1.5:1 Base:PS-Y, $CHCl_3$;<br>1.5:1 Base:PS-Y, $CHCl_3$ | Amide<br>Ester<br>Thioester |
| Thiol | PS-SH | Oxidant, $CHCl_3$ | Disulfide |

*Opt = optional; NHS = N-hydroxy succinimide; ITC = isothiocycanate; IC = isocyanate

TABLE 3

X and Z pairings of PS(L)-NP-X or NP-X alone and TA-Z for covalent conjugation [to make PS(L)-NP-TA the preferred material or NP-TA alone]

| PS(L)-NP-X (or NP-X) | TA-Z | Conditions | Covalent Bond |
|---|---|---|---|
| Alkyl Halide (Chlorine) | TA-OH<br>TA-SH<br>TA-COOH<br>$TA-NH_2$ | Base, $CHCl_3$ or DMSO | Ether<br>Thio Ether<br>Ester |
| Acyl Halide (Chlorine) | $TA-NH_2$<br>TA-SH<br>TA-OH<br>TA-Phenyl | 1.5:1 Base:PS-Y (Opt) $CHCl_3$ or DMSO | Amide<br>Thio Ester<br>Ester<br>Ketone |
| Aromatic (Phenyl) | TA-Cl<br>TA-COCl | $AlCl_3$, $CHCl_3$ or DMSO | Alkyl chain<br>ketone |
| Aromatic (Halide Phenyl) | $TA-NH_2$<br>TA-OH<br>TA-SH | Base, $CHCl_3$ or DMSO | Secondary Amine<br>Ether<br>Thioether |
| Carboxylic Acid | TA-OH<br>$TA-NH_2$<br>TA-Cl<br>TA-SH | Acid, $CHCl_3$ or DMSO;<br>Acid, $CHCl_3$ or DMSO;<br>Base, $CHCl_3$ or DMSO;<br>Acid, $CHCl_3$ or DMSO | Ester<br>Amide<br>Ester<br>Thioester |
| Sulfonic Acid | TA-OH<br>$TA-NH_2$<br>TA-SH | 1.5:1 Base:PS-Y $PCl_5$, $CHCl_3$ or DMSO;<br>$SOCl_2$ may also be used | Sulfonic ester<br>Amino Sulfonate<br>Sulfonic thioester |
| Phosphoric Acid | TA-OH<br>$TA-NH_2$<br>TA-SH | 1.5:1 Base:PS-Y $SOCl_2$, $CHCl_3$ or DMSO | Phosphoramidite |
| Alcohol (Primary) | TA-Cl<br>TA-COOH<br>TA-ester<br>TA-thioester<br>TA-anhydride<br>TA-CHO<br>TA-ITC<br>TA-IC | Base, $CHCl_3$ or DMSO;<br>Base, $CHCl_3$ or DMSO;<br>Base, $CHCl_3$ or DMSO;<br>Base, $CHCl_3$ or DMSO;<br>Base, $CHCl_3$ or DMSO;<br>Base, Pd catalyst, $CHCl_3$;<br>1.5:1 Base:PS-Y, $CHCl_3$;<br>1.5:1 Base:PS-Y, $CHCl_3$ | Ether<br>Ester<br>Ester<br>Ester<br>Ester<br>Ester<br>Thiocarbamate<br>Urethane |
| Maleimide (Mal) | TA-SH | pH 6-8 in water;<br>1.5:1 Base:PS-Y in organic solvent | Thioether |
| Ester | $TA-NH_2$<br>TA-OH<br>TA-SH | Acid, $CHCl_3$ or DMSO | Amide<br>Ester<br>Thioester |

TABLE 3-continued

X and Z pairings of PS(L)-NP-X or NP-X alone and TA-Z for covalent conjugation [to make PS(L)-NP-TA the preferred material or NP-TA alone]

| PS(L)-NP-X (or NP-X) | TA-Z | Conditions | Covalent Bond |
|---|---|---|---|
| Thiol | TA-Mal | pH 6-8 in water; | Thioether |
| | TA-ITC | 1.5:1 Base:PS-Y, | Dithiocarbamate |
| | TA-IC | $CHCl_3$; | Thiourethane |
| | | 1.5:1 Base:PS-Y, | |
| | | $CHCl_3$ | |
| Azide | TA-Alkyne | Cu(I), $CHCl_3$ or | Triazole |
| | | DMSO; | |
| | | Cu free, $CHCl_3$ or | |
| | | water | |
| Aldehyde | TA-NH2 | CuI, TBHP, CHCl3; | Amide |
| | TA-OH | Base, Pd catalyst, | Ester |
| | | $CHCl_3$; | |
| Alkene | TA-Diene | Diels-Alder | Cyclo-alkyl |
| Alkyne | TA-Azide | Cu(I), $CHCl_3$ or | Triazole |
| | | DMSO; | |
| | | Cu free, $CHCl_3$ or | |
| | | water | |
| isocyanate | TA-OH | Base, $CHCl_3$; | Urethane |
| | TA-$NH_2$ | $CHCl_3$; | Urea |
| | TA-SH | Base, $CHCl_3$ | Thiourethane |
| isothiocyanate | TA-SH | 1.5:1 Base:PS-Y, | Dithiocarbamate |
| | TA-$NH_2$ | $CHCl_3$; | Thiourea |
| | TA-OH | pH 7.4 in water; | Thiocarbamate |
| | | 1.5:1 Base:PS-Y, | |
| | | $CHCl_3$ | |
| Amine | TA-COOH | Acid, $CHCl_3$ or | Amide |
| (A) | TA-COCl | DMSO; | Amide |
| | TA-NHS | Base (Opt), $CHCl_3$ | Amide |
| | TA-CHO | pH 7.4 in water; | Amide |
| | TA-ITC | Base, Pd catalyst, | Thiourea |
| | TA-IC | $CHCl_3$; | Urea |
| | | pH 7.4 in water; | |
| | | pH 7.4 in water | |
| Anhydride | TA-$NH_2$ | CHCl3 or DMSO; | Amide |
| | TA-OH | 1.5:1 Base:PS-Y, | Ester |
| | TA-SH | $CHCl_3$; | Thioester |
| | | 1.5:1 Base:PS-Y, | |
| | | $CHCl_3$ | |
| Thiol | TA-SH | Oxidant, $CHCl_3$ | Disulfide |

*Opt = optional; NHS = N-hydroxy succinimide; ITC = isothiocycanate; IC = isocyanate

TABLE 4

Q and Z pairings of PS-L-Q and TA-Z for covalent conjugation [This makes PS(L)-TA, that could potentially be used (no NP) or could then be attached to the NP to form a new (and never tried) form PA-TS-NP]

| PS-L-Q | TA-Z | Conditions | Covalent Bond |
|---|---|---|---|
| Alkyl Halide | TA-OH | Base, $CHCl_3$ or | Ether |
| (Chlorine) | TA-SH | DMSO | Thio Ether |
| | TA-COOH | | Ester |
| | TA-$NH_2$ | | |
| Acyl Halide | TA-$NH_2$ | 1.5:1 Base:PS-Y (Opt) | Amide |
| (Chlorine) | TA-SH | $CHCl_3$ or DMSO | Thio Ester |
| | TA-OH | | Ester |
| | TA-Phenyl | | Ketone |
| Aromatic | TA-Cl | $AlCl_3$, $CHCl_3$ or | Alkyl chain |
| (Phenyl) | TA-COCl | DMSO | ketone |
| Aromatic | TA-$NH_2$ | Base, $CHCl_3$ or | Secondary Amine |
| (Halide Phenyl) | TA-OH | DMSO | Ether |
| | TA-SH | | Thioether |
| Carboxylic Acid | TA-OH | Acid, $CHCl_3$ or | Ester |
| | TA-$NH_2$ | DMSO; | Amide |
| | TA-C1 | Acid, $CHCl_3$ or | Ester |
| | TA-SH | DMSO; | Thioester |
| | | Base, $CHCl_3$ or | |
| | | DMSO; | |
| | | Acid, $CHCl_3$ or | |
| | | DMSO | |

TABLE 4-continued

Q and Z pairings of PS-L-Q and TA-Z for covalent conjugation [This makes PS(L)-TA, that could potentially be used (no NP) or could then be attached to the NP to form a new (and never tried) form PA-TS-NP]

| PS-L-Q | TA-Z | Conditions | Covalent Bond |
|---|---|---|---|
| Sulfonic Acid | TA-OH<br>TA-$NH_2$<br>TA-SH | 1.5:1 Base:PS-Y<br>$PCl_5$, $CHCl_3$ or<br>DMSO;<br>$SOCl_2$ may also be<br>used | Sulfonic ester<br>Amino Sulfonate<br>Sulfonic thioester |
| Phosphoric Acid | TA-OH<br>TA-$NH_2$<br>TA-SH | 1.5:1 Base:PS-Y<br>$SOCl_2$, $CHCl_3$ or<br>DMSO | Phosphoramidite |
| Alcohol<br>(Primary) | TA-Cl<br>TA-COOH<br>TA-ester<br>TA-thioester<br>TA-anhydride<br>TA-CHO<br>TA-ITC<br>TA-IC | Base, $CHCl_3$ or<br>DMSO;<br>Base, $CHCl_3$ or<br>DMSO;<br>Base, $CHCl_3$ or<br>DMSO;<br>Base, $CHCl_3$ or<br>DMSO;<br>Base, $CHCl_3$ or<br>DMSO;<br>Base, Pd catalyst,<br>$CHCl_3$;<br>1.5:1 Base:PS-Y,<br>$CHCl_3$;<br>1.5:1 Base:PS-Y,<br>$CHCl_3$ | Ether<br>Ester<br>Ester<br>Ester<br>Ester<br>Ester<br>Thiocarbamate<br>Urethane |
| Maleimide<br>(Mal) | TA-SH | pH 6-8 in water;<br>1.5:1 Base:PS-Y in<br>organic solvent | Thioether |
| Ester | TA-$NH_2$<br>TA-OH<br>TA-SH | Acid, $CHCl_3$ or<br>DMSO | Amide<br>Ester<br>Thioester |
| Thiol | TA-Mal<br>TA-ITC<br>TA-IC | pH 6-8 in water;<br>1.5:1 Base:PS-Y,<br>$CHCl_3$;<br>1.5:1 Base:PS-Y,<br>$CHCl_3$ | Thioether<br>Dithiocarbamate<br>Thiourethane |
| Azide | TA-Alkyne | Cu(I), $CHCl_3$ or<br>DMSO;<br>Cu free, $CHCl_3$ or<br>water | Triazole |
| Aldehyde | TA-NH2<br>TA-OH | CuI, TBHP, CHCl3;<br>Base, Pd catalyst,<br>$CHCl_3$; | Amide<br>Ester |
| Alkene | TA-Diene | Diels-Alder | Cyclo-alkyl |
| Alkyne | TA-Azide | Cu(I), $CHCl_3$ or<br>DMSO;<br>Cu free, $CHCl_3$ or<br>water | Triazole |
| isocyanate | TA-OH<br>TA-$NH_2$<br>TA-SH | Base, $CHCl_3$;<br>$CHCl_3$;<br>Base, $CHCl_3$ | Urethane<br>Urea<br>Thiourethane |
| isothiocyanate | TA-SH<br>TA-$NH_2$<br>TA-OH | 1.5:1 Base:PS-Y,<br>$CHCl_3$;<br>pH 7.4 in water;<br>1.5:1 Base:PS-Y,<br>$CHCl_3$ | Dithiocarbamate<br>Thiourea<br>Thiocarbamate |
| Amine<br>(A) | TA-COOH<br>TA-COCl<br>TA-NHS<br>TA-CHO<br>TA-ITC<br>TA-IC | Acid, $CHCl_3$ or<br>DMSO;<br>Base (Opt), $CHCl_3$<br>pH 7.4 in water;<br>Base, Pd catalyst,<br>$CHCl_3$;<br>pH 7.4 in water;<br>pH 7.4 in water | Amide<br>Amide<br>Amide<br>Amide<br>Thiourea<br>Urea |
| Anhydride | TA-$NH_2$<br>TA-OH<br>TA-SH | CHCl3 or DMSO;<br>1.5:1 Base:PS-Y,<br>$CHCl_3$;<br>1.5:1 Base:PS-Y,<br>CHCh | Amide<br>Ester<br>Thioester |
| Thiol | TA-SH | Oxidant, $CHCl_3$ | Disulfide |

*Opt = optional; NHS = N-hydroxy succinimide; ITC = isothiocyanate; IC = isocyanate Nanocompositions for PDT were evaluated and enhanced. Photodynamic therapy (PDT) is the ablation of tissue through oxidative stress, triggered by exposing a target area to a photo-sensitive agent (photosensitizer, PS) and illuminating it with the correct wavelength of light. The oxidative stress is triggered by the PS absorbing light and using it to produce reactive oxygen species (ROS). There are two requirements for a dye to qualify as a PS: 1) efficient conversion of electrons to long lived triplet states, and 2) possessing a triplet state of high enough energy to mediate the process.

Figure 7:
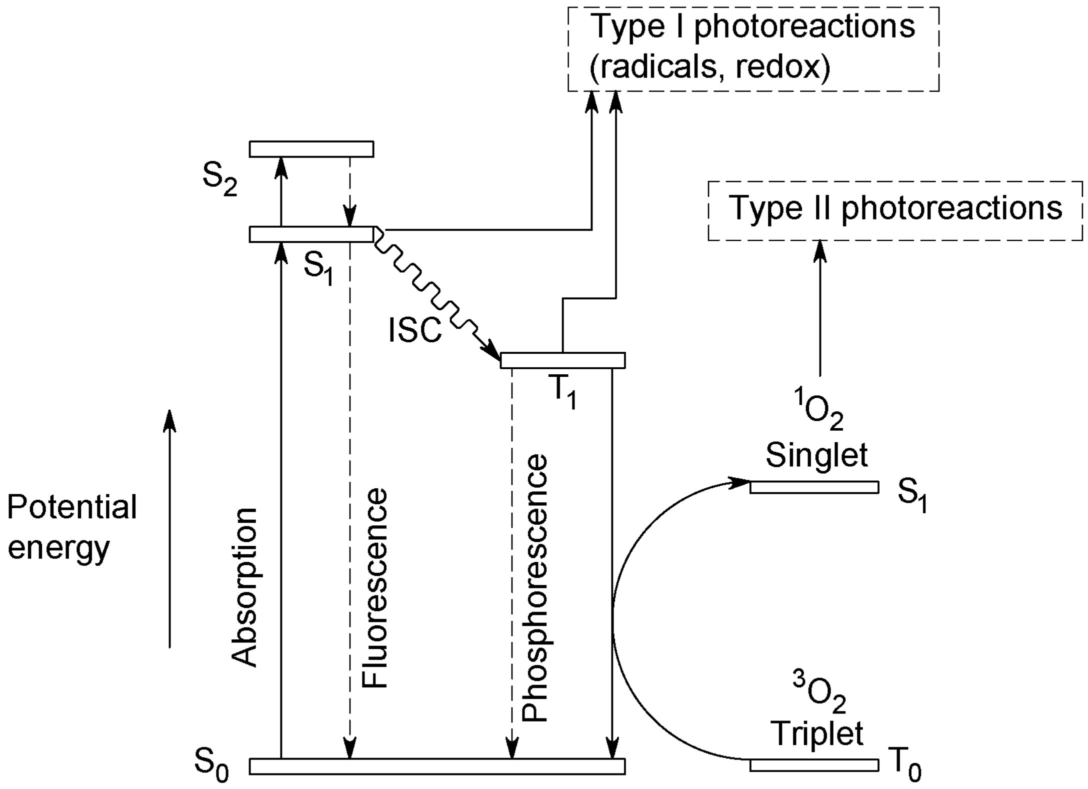
FIG. 7 shows a simple mechanical overview of how a PS utilizes light to generate ROS and some example PS core structures

FIG. 7 shows a simple mechanical overview of how a PS utilizes light to generate ROS and some example PS core structures. There are a number of other features to consider in selecting a practical PS (useful in clinical PDT), but these two are the bare minimum in selecting a dye to qualify as a PS.

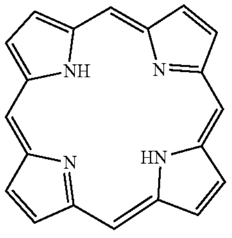

Porphyrin

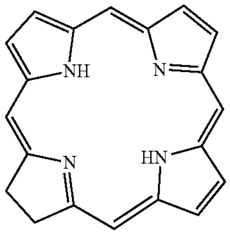

Chlorin

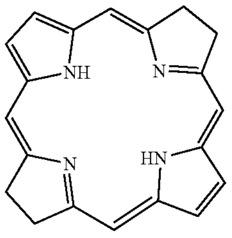

Bacteriochlorin

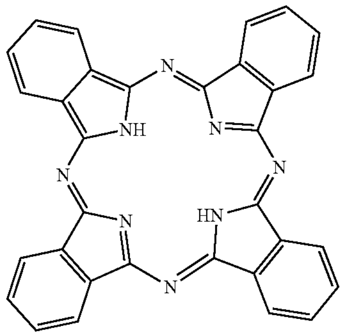

Phthalocyanine

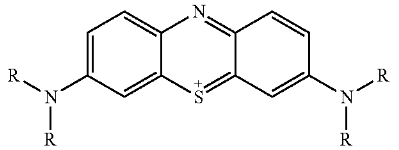

Phenothiazinium

-continued

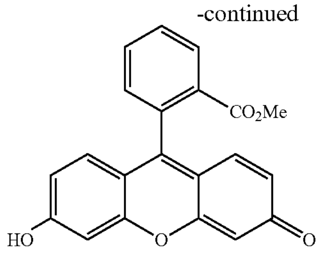

Xanthene

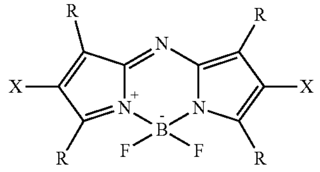

BODIPY

FIG. 7: Left=A simple Jablonski diagram of a PS generating ROS. S=singlet, T=triplet, ISC=intersystem crossing, Right=Example PS core structures.

A PS will absorb light of a suitable wavelength to transition an electron from the ground state ($S_0$) to a higher position singlet state ($S_1$, $S_2$, etc. . . . ). From the singlet state, the electron will undergo a process known as an intersystem crossing (ISC), where its spin will invert, and degrade to an energetically lower position, the triplet state ($T_1$).

It is an understood feature of photo-physics that electrons will degrade to the lowest possible position before fluorescing or phosphorescing (El-Sayed's Rule). Therefore, it is assumed electrons will mechanistically speaking end up in the $S_1$ or $T_1$ states. The wavelength employed in photoexcitation will also typically correspond to the $S_0 \rightarrow S_1$ transition as well.

In the $T_1$ state, there are four possible outcomes: 1) Phosphorescence, 2) internal conversion (loss of the excited state by dumping the energy as heat), 3) direct redox of the $T_1$ with a local scaffold, and 4) excitation of oxygen from the ground triplet state to the singlet.

The (3) and (4) processes are known as Type 1 and Type 2 [ROS] production. Type 2 ROS refers specifically to singlet oxygen, while Type 1 encompasses every other possible species (e.g. hydroxyl radical, superoxide anion, and peroxides). Type 1 and 2 ROS are mainly distinguished by the mechanism of action; all Type 1 ROS is a product of electron transfer, and Type 2 is not.

In clinical PDT, criteria for a practical PS may be embodied by the following characteristics: high photo-stability, water soluble, large absorption cross-section, having a suitable lambda max, and producing an ideal mix of Type 1/2 ROS. All these features together constitute a PS that has longevity and potency in PDT.

The mixture of Type 1/2 ROS generated is perhaps the most important. Radicals are among the most commonly formed products of Type 1 ROS production, and thus owing to their high instability, have very small diffusion lengths. Type 2 ROS may diffuse as far as 0.20 μm, giving it a far greater range than the highly unstable Type 1 radicals, which will typically react with the first things they encounter.[4] Thus, a tissue will be increasingly sensitive to PDT when the PS employed predominantly generates Type 2 ROS.

In addition, it is also worth mentioning that the mixture of Type 1/2 ROS will affect the longevity of a PS. As Type 1 ROS production is a direct redox process of the $T_1$, a PS is at greater risk of oxidizing. (see photostability below). By employing a PS that predominantly produces Type 2 ROS, the PS can undergo a greater total of turnovers before degrading.

Clinically viable PDT requires a concentration of 0.5-1.0 mM Type 2 ROS (singlet oxygen) being produced.[3] Therefore, the ideal practical PS would have a minimum of Type 1 ROS character, maximum of Type 2, and be capable of reaching the Type 2 ROS concentration necessary for treatment.

Furthermore, the PS must be soluble in its method of delivery; if the PS aggregates, then all excited states will end up being quenched and thus produce zero Type 1 or 2 ROS. The high solubility will also raise the threshold concentration where PS-PS interactions may increasingly occur. These interactions are typically intramolecular ones that can lead to excited state quenching.

In examples, photostability of the chosen PS is required to reach the above-mentioned concentration of 0.5-1.0 mM Type 2 ROS. Type 1/2 ROS generation can play a part in this, but here it is predominantly referred to as simply the stability of the PS itself in the excited state. Potential routes of bleaching may be cleaving of covalent bonds or non-specific interactions with the environment while in the excited state. As an example, fluorescein is a fluorophore that produces no ROS, but is known to somewhat easily photobleach. The excited state stability therefore becomes an important aspect of consideration, where it is desired to be high enough such that the necessary number of turnovers will yield the required Type 2 ROS concentration.

As an example, a 2 μM PS will require a minimum of 250 Type 2 ROS turnovers, assuming an ideal system. When considered as a real system, the total number of turnovers per PS will increase due to the events that yield no ROS, Type 1 ROS, or result in photobleaching and thus decreasing the available PS population.

Discussed further below is cross-section absorption for a PS. Following the stability and Type 1/2 ROS mix, an ideal practical PS must also turnover at a suitable rate. PDT by its nature is to induce oxidative stress on tissue. Thus, the Type 1/2 ROS production rate must exceed a tissue's ability to compensate. The production rate will be largely influenced by the PS excited state population.

In general terms, the excited state population of any dye would be controlled by: temperature, concentration of dye, flux of incident light, pathlength, and the absorption cross-section of the dye (epsilon). Of these factors, epsilon is the only one that is a feature of the dye itself. Therefore, epsilon is an important point of consideration in controlling the rate of Type 1/2 ROS production. A low epsilon will hamper the ROS production rate, possibly increasing the total concentration of Type 2 ROS necessary to treat.

Figure 8:
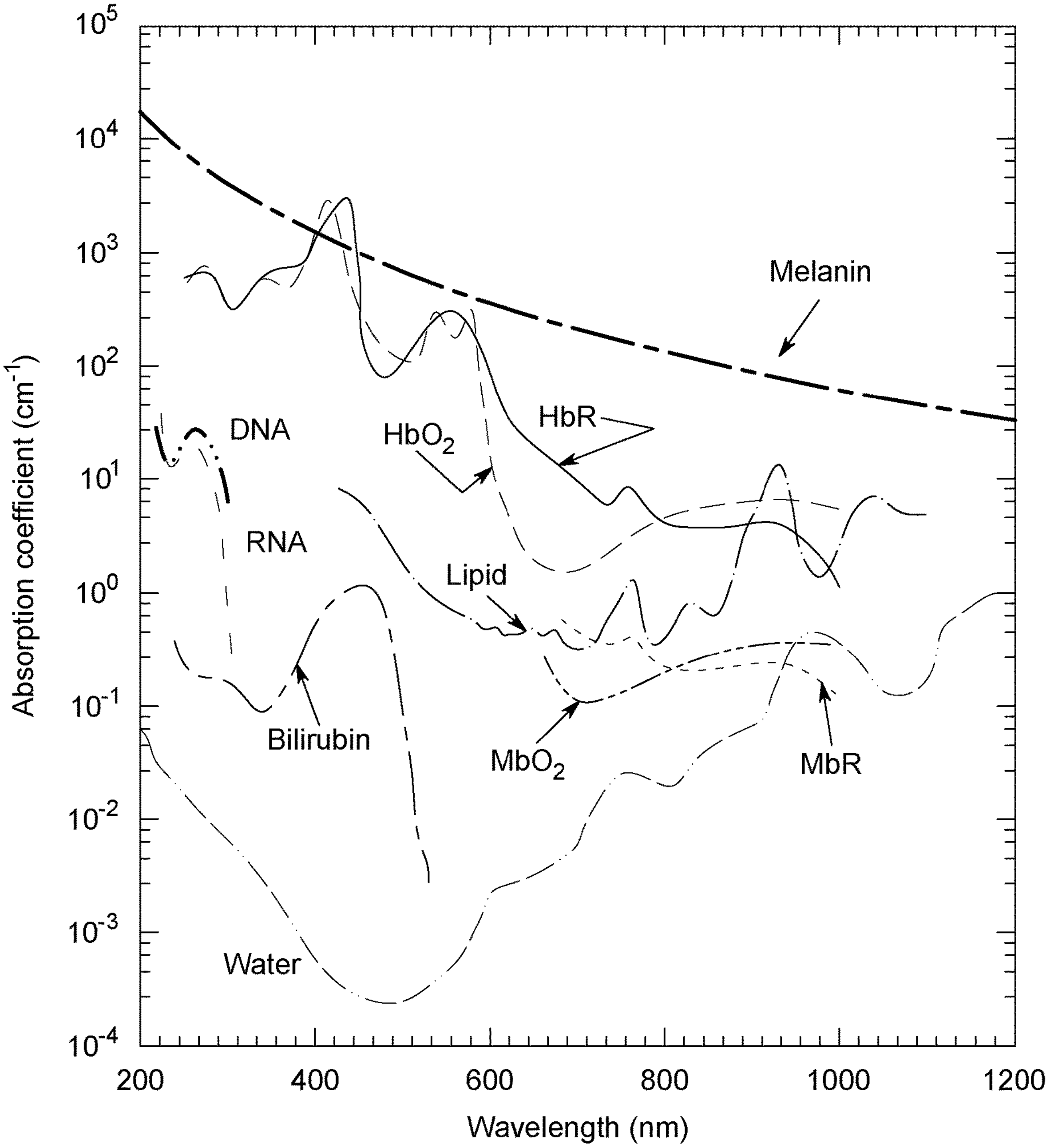
FIG. 8 is a graph illustrating various contributions to optical density by tissue in vivo, wherein HbO2=oxy-hemoglobin, HbR=deoxy-hemoglobin, MbO2=oxy-myoglobin, and MbR=deoxy-myoglobin.

Lastly, viable practical PDT in tissue may utilize a lambda max that is contained in the first optical window, where photons travel maximally through tissue with minimal scattering or body absorption. This leads to the most number photons, at the greatest possible depth, being available for a PS to mediate PDT (directly influences excited state population at specific depths via changes in flux). The first optical window for PDT can be defined as being between 650-850 nm. FIG. 8 shows the wavelength dependent penetration depth of light through tissue.

Discussed below are evaluations methods and system for evaluating a PS for Type 1/2 Production. The above describes the parameters that would best define an ideal practical PS. However, they do not describe how to evaluate the best PS in a given set with these common attributes. This can be semi-quantitatively analyzed using fluorescent molecular probes that scavenge Type 1/2 ROS. Two specific probes ideal for this are 9,10-anthracene bis(methylene) dimalonic acid (ADMA) and singlet oxygen sensor green (SOSG).

Anthracene and its derivatives are sensitive to both Type 1 and Type 2 ROS, while SOSG is specifically for Type 2 ROS studies.[9] By tracking the fluorescent changes of these probes over time, the Type 1/2 ROS and rates of production by a set of PSs can be directly compared in a semi-quantitative manner. In the work to follow, AMDA is the anthracene derivative utilized.

ADMA decays according to first order rate law kinetics. As such, the rate of total Type 1 and 2 ROS may be studied by tracking its fluorescence loss over time as a natural log, yielding a linear plot whose slope is the rate constant of Type 1 and 2 ROS production (referred to as the k-value). The greater the rate constant, the more Type 1 and Type 2 ROS being produced, and thus PSs compared under identical conditions (equivalent [PS], [$O_2$], flux, temp) can be semi-quantitatively compared.

SOSG functions in a manner opposite to that of the anthracene probe; instead of a fluorescence loss, SOSG experiences a fluorescence enhancement when interacting with Type 2 ROS; Type 1 ROS has no effect. Taking a ratio of the current fluorescent signal to its initial, plotted against time, yields a linear plot; no changes occur upon illumination without a PS present. Therefore, the steeper the slope (S-value), the more Type 2 ROS being produced.

Combining the findings of the SOSG and ADMA tests, semi-quantitative comparisons and estimates about the performance of PSs in a given set may be extrapolated, when performed under identical conditions (equivalent [PS], [$O_2$], flux, temp). This will aid in choosing a PS that maximizes PDT efficacy by showing it has a minimum of Type 1 ROS and maximum of Type 2 ROS production, while also producing at a sufficient rate to efficiently ablate tissue.

The exact method of study is as follows, using a factory default Horiba Duetta:

3. Pulse the molecular probe for initial fluorescence
   a. Simple fluorescence scan
   b. ADMA Ex=380 nm, tracked from 390-600 nm
   c. SOSG Ex=504 nm, tracked from 515-650 nm.
   d. Ex/Em slits for both=2/3 nm, Integration for 1 second, 5 scans
   e. The peak of highest counts is used
2. The PS is illuminated using the wavelength of its maxima for a set amount of time
   a. Fixed wavelength fluorescent study mode; choose a time point desired
   b. Ex/Em bandwidth=10/1 nm
4. Pulse the molecular probe for fluorescent changes
5. Repeat Steps 2 and 3 until the range time values desired is covered
6. Treat the data
   a. Anthracene=$\mathrm{Ln}(I/I_0)$ vs time; slope=k-value
   b. SOSG=$I/I_0$ vs time; slope=S-value Using a PS as an assigned origin (standard by which all other PSs are compared to), any PS may be charted by comparing the k and S-values ($k/k_{std}$=k', $S/S_{std}$=S', k"=1-k', S"=S'-1) at clinically relevant concentrations (1-2 μM). By plotting the k" and S" values as x,y coordinates (respectively), the semi-quantitative comparison of PSs against each other may be directly visualized; the origin PS will have a position of 0,0. The x-axis will then stretch from $-\infty$ to 1, and y-axis from $-1$ to $\infty$.

Figure 9:
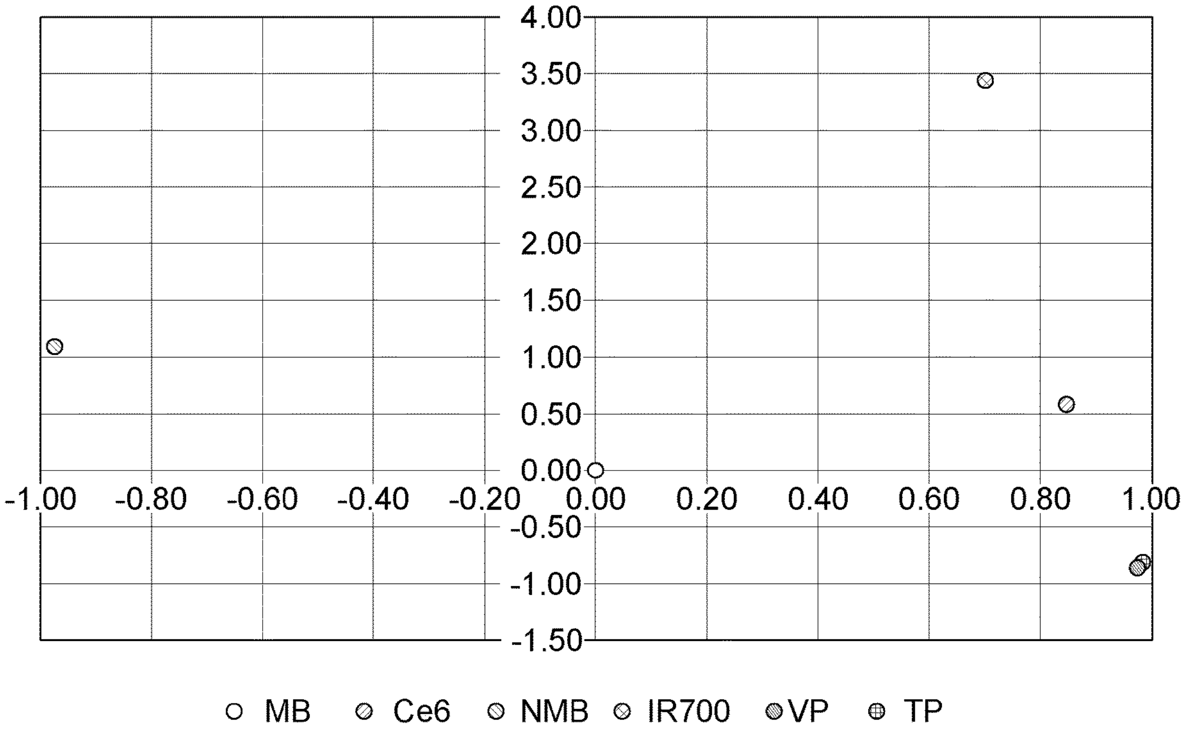
FIG. 9 illustrates a grid for PS treatment options.

FIG. 9 illustrates a grid. The grid is separated into four segments allows us to coin four classes of PSs: Class A (top right), Class B (top left), Class C (bottom left), and Class D (bottom right). These assignments were made on the basis of having preferential treatment for a PS who produces mostly Type 2 ROS in totality, going in a descending order to very little ROS overall. Class A PSs are thus to most desirable.

Methylene blue (MB) was chosen as a standard for its high characterization in the literature. NMB=New Methylene Blue, Ce6=Chlorin e6, VP=Verteporfin, TP=Temoporfin.

| [PS] E-6 | k (E-4) $s^{-1}$ | S E−2 $s^{-1}$ | k' | S' | k'' | S'' |
|---|---|---|---|---|---|---|
| MB | 6.13 | 0.46 | 1 | 1 | 0.00 | 0.00 |
| Ce6 | 0.94 | 0.73 | 0.153 | 1.59 | 0.85 | 0.59 |
| NMB | 12.1 | 0.96 | 1.97 | 2.09 | −0.97 | 1.09 |
| IR700 | 1.83 | 2.04 | 0.299 | 4.43 | 0.70 | 3.43 |
| Verteporfin | 0.16 | 0.06 | 0.03 | 0.13 | 0.97 | −0.87 |
| Temoporfin | 0.10 | 0.08 | 0.02 | 0.17 | 0.98 | −0.83 |

After having evaluated a selection of PSs for the ideal performer, the chosen candidate may then be further enhanced via attachment to a nanoparticle (NP). It is commonly understood within the world of academic PDT that coupling a PS with a NP yields enhanced performance, such as: heightened solubility, increased photo-stability, modulated pharmacokinetics, and diminished PS-PS interactions. 8-arm polyethylene glycol (8PEG) is a macropolymer construct that can be used as a NP and has been shown to function in such a capacity. The PS chlorin e6 (Ce6) had markedly enhanced solubility in aqueous media, improved k-values when covalently conjugated to the amine derivatized version of 8PEG (8PEGA), and a regulated pharmacokinetic profile. This is supported in the evaluation of IR700 conjugated to 8PEGA.

Figure 10A:
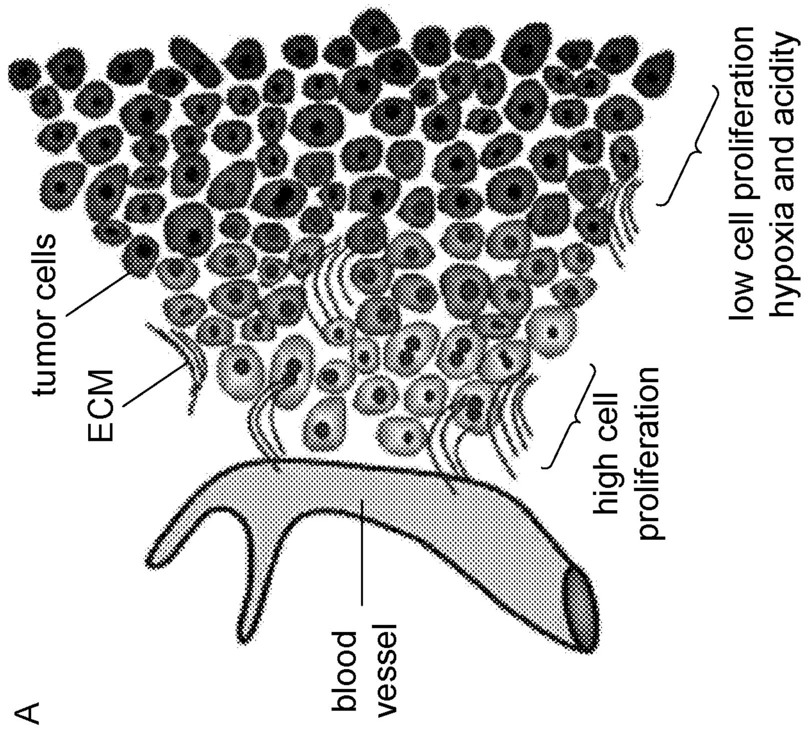
FIG. 10A illustrates a cartoon of tumor cell proliferation with respect to vasculature proximity.
Figure 10B:
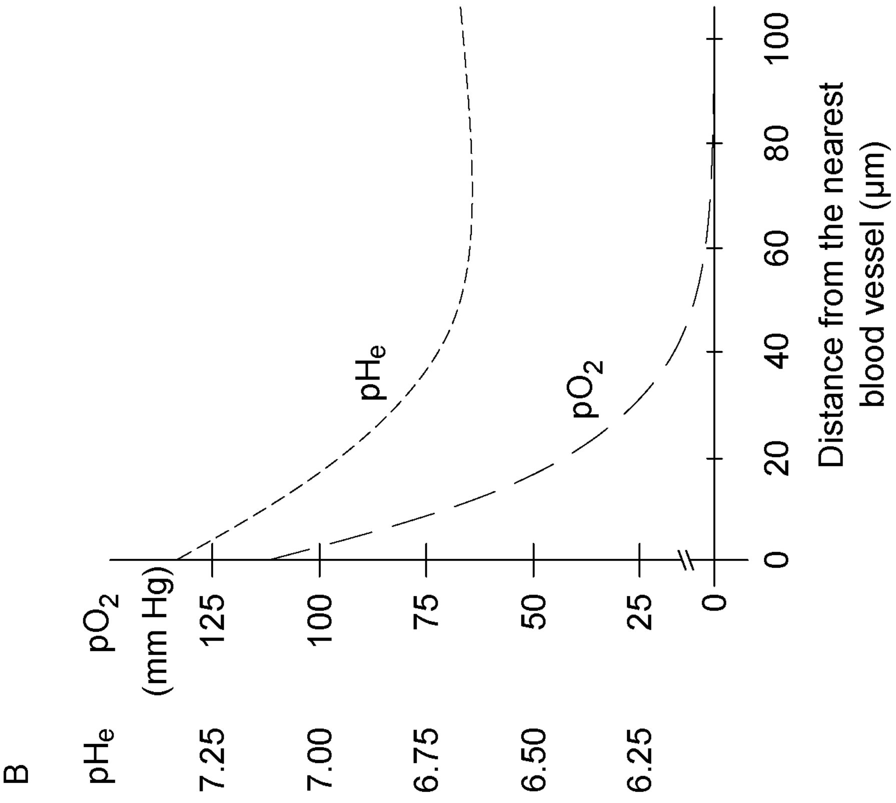
FIG. 10B is a graph that shows quantification of tumor oxygenation with respect to vasculature proximity; Dotted line=extracellular pH, Dashed=tumor oxygenation.

Tumor hypoxia as a result of unchecked tissue growth. FIG. 10A illustrates a cartoon of tumor cell proliferation with respect to vasculature proximity. FIG. 10B is a graph that shows quantification of tumor oxygenation with respect to vasculature proximity; Dotted line=extracellular pH, Dashed=tumor oxygenation.

IR700 can be loaded to 8PEGA via an amine to N-hydroxy succinimide reaction that is spontaneous at room temperature in aqueous, mildly basic media (pH 7.4). This reaction yields a highly stable amide linkage between the PS and 8PEGA. First, IR700 is dissolved in a 1% water containing solution of DMSO (2 mg/mL). Triethyl amine is added in a 1:1 mol ratio to deprotonate the carboxyl groups. Then, fresh disuccinimydal carbonate (DSC) in DMSO (100 uL) is added in a mol ration of 0.95:1 DSC:IR700 under stirring and left for 1 hour. The resulting formed NHS-ester IR700 is then added dropwise to a 20 mg/mL solution of 8PEGA in 0.01M phosphate buffered saline (PBS), and allowed to react overnight in the dark.

The next day, the reaction liquid is removed and centrifuged using a MW exclusion filter (MW depending on 8PEGA used) and pure water. Centrifuging continues until no IR700 is visually detected in the filtered liquids (UV-VIS will show ABS<0.05). The isolated PEG-IR700 solution is then frozen in liquid nitrogen and lyophilized to obtain a dry solid. The shelf life is years when stored at −20° C. and in the dark.

The following examples are provided to illustrate various embodiments of systems, processes, compositions, applications and materials of the present inventions. These examples are for illustrative purposes, may be prophetic, and should not be viewed as, and do not otherwise limit the scope of the present inventions.

| | IR700 | | PEG-IR700 (40 kDa) | | PEG-IR700 (20 kDa) | | PEG-IR700 (High Load) | |
|---|---|---|---|---|---|---|---|---|
| [PS]/ k-vlaue (E-4) | 3.99E−06 | 2.62 | 3.99E−06 | 2.92 | 3.95E−06 | 2.73 | 4.68E−06 | 2.25 |
| [PS]/ SOSG (E-2) | 3.91E−06 | 2.89 | 4.07E−06 | 3.13 | 4.01E−06 | 3.03 | — | — |

Conjugation of IR700 to 8PEGA of varied loading or MW demonstrated modulation of the PS performance; k and S-values tended to increase with conjugation to larger MW PEGs. In addition, when increasing the loading of the largest MW 8PEGA (40 kDa, IR700:8PEGA mols) from ~1.75:1 to ~2.70:1, there is a remarkable decrease in PS performance. Therefore, there is an optimal loading ratio to 8PEGA; delivering enough PS, without significantly compromising its ability to perform.

Conjugation of a PS to 8PEGA will increase performance by forcefully segregating them, preventing PS-PS interactions. Therefore, it stands to reason that a higher loading will increase the probability of PS-PS interactions and display a corresponding decrease in performance (shown above).

Additionally, 8PEGA can be considered a superior NP for application in PDT, as the PS loaded to each of its arms is in direct contact with the oxygenated environment. This avoids the issue of oxygen needing to diffuse into a NP, and Type 1 or 2 ROS diffusing out, leading to efficient usage of local oxygen in the present environment. This is especially important in oncological applications where hypoxia can be an issue. FIGS. 10A and 10B shows the degree of oxygenation in a tumor as a function of distance from vasculature.

Example 1

IR700 DX covalently attached to a small nanostructure (less than or equal to 25 nm in hydrodynamic diameter).

A dosing of less than or equal to 450 mg/kg particle in humans.

A therapeutic dosage of light administered that does not exceed 85% of the power that would yield thermal breakdown.

The use of IR700 DX as both a therapeutic or imaging agent.

Optionally attaching secondary imaging agents that may be fluorophores or radioagents (e.g. technetium).

Where a peptide, protein, antibody, small molecule, or otherwise any other entity that would act as a targeting agent to cardiac tissue is attached to the nanostructure.

Use of linear and multi-armed PEGs, but may also include any structure or material that fulfills the less than or equal to 25 nm hydrodynamic diameter feature (e.g. polyamido amine dendrimers, PAMAM).

Example 2

Use of linear PEG, in the embodiment of Example 1. Other structures such as any structure or material that fulfills the less than or equal to 25 nm hydrodynamic diameter feature (e.g. polyamido amine dendrimers, PAMAM) may be used.

Example 3

Use of multi-arm PEGs, for the embodiment of Example 1. Other structures, such as any structure or material that fulfills the less than or equal to 25 nm hydrodynamic diameter feature (e.g. polyamido amine dendrimers, PAMAM).

Example 4

A method of forming an IR700-NP-CTP nanocomposition is to attach the IR700 to the NP, in the required ratio (e.g., 1-3 per NP) and to then attach a linker to the IR700 that have been attached to the NP. The TA, a PEP is then attached to this linker, as well as potentially other arms of the NP.

Example 5

A PS-NP-TA nanocomposition, where PS is a phthalocyanine dye and the NP is 8PEG, 8PEGA, or 8PEGMAL and combinations of these, and the TA is a PEP.

Example 6

A PS-NP-TA nanocomposition, where PS is a phthalocyanine dye and the NP is 8PEG, 8PEGA, or 8PEGMAL and combinations of these, and the TA is a CTP. The nanocomposition having a hydrodynamic diameter (e.g., size) of 25 nm and less, a hydrodynamic diameter of 10 nm and less, and having a hydrodynamic diameter of from about 30 nm to about 5 nm, and having a hydrodynamic diameter of from about 20 nm to about 5 nm, and being 20 kilodaltons (kDa) and greater, that are 40 kDa and greater, and that are from about 15 kDa to about 50 kDa, and that are about 5 kDa to about 100 kDa.

Example 7

A PS-NP-TA nanocomposition, where PS is IR700 and the NP is 8PEG, 8PEGA, or 8PEGMAL and combinations of these, and the TA is one or more of a PEP, a protein, a small molecule, iRGD, RGD, and the peptides and compositions taught and disclosed in US Patents and Applications Nos. 2009/0246133, 2009/0226372, U.S. Pat. Nos. 9,115,170, and 10,370,245 the entire disclosure of each of which are incorporated herein by reference.

Example 8

A PS-NP-TA nanocomposition, where PS is IR700 and the NP is 8PEG, 8PEGA, or 8PEGMAL and combinations of these, and the TA is one or more of a PEP, a protein, a small molecule, iRGD, RGD, and the peptides and compositions taught and disclosed in US Patents and Applications Nos. 2009/0246133, 2009/0226372, U.S. Pat. Nos. 9,115,170, and 10,370,245 the entire disclosure of each of which are incorporated herein by reference. The nanocomposition having a hydrodynamic diameter (e.g., size) of 25 nm and less, a hydrodynamic diameter of 10 nm and less, and having a hydrodynamic diameter of from about 30 nm to about 5 nm, and having a hydrodynamic diameter of from about 20 nm to about 5 nm, and being 20 kilodaltons (kDa) and greater, that are 40 kDa and greater, and that are from about 15 kDa to about 50 kDa, and that are about 5 kDa to about 100 kDa.

Example 9

A PS-NP-TA nanocomposition, where PS is IR700 and the NP is 8PEG, 8PEGA, or 8PEGMAL and combinations of these, and the TA is one or more of a PEP, a protein, a small molecule, iRGD, RGD, and the peptides and compositions taught and disclosed in US Patents and Applications Nos. 2009/0246133, 2009/0226372, U.S. Pat. Nos. 9,115,170, and 10,370,245 the entire disclosure of each of which are incorporated herein by reference.

Example 10

A PS-NP-TA nanocomposition, where PS is IR700 and the NP is 8PEG, 8PEGA, or 8PEGMAL and combinations of these, and the TA is one or more of a PEP, a protein, a small molecule, iRGD, RGD, and the peptides and compositions taught and disclosed in US Patents and Applications Nos. 2009/0246133, 2009/0226372, U.S. Pat. Nos. 9,115,170, and 10,370,245 the entire disclosure of each of which are incorporated herein by reference. The nanocomposition having a hydrodynamic diameter (e.g., size) of 25 nm and less, a hydrodynamic diameter of 10 nm and less, and having a hydrodynamic diameter of from about 30 nm to about 5 nm, and having a hydrodynamic diameter of from about 20 nm to about 5 nm, and being 20 kilodaltons (kDa) and greater, that are 40 kDa and greater, and that are from about 15 kDa to about 50 kDa, and that are about 5 kDa to about 100 kDa.

Example 11

The embodiments of Examples 1 to 10, in which the NP is a 6PEG, 6PEGA, or 6PEGMAL and combinations of these instead of 8PEG.

Example 12

The embodiments of Examples 1 to 10, in which the NP is a 4PEG, 4PEGA, or 4PEGMAL and combinations of these, instead of 8PEG.

Example 13

The embodiments of Examples 1 to 10, in which the nanocomposition has one or more of the following parameters: from 1 to 2 PSs per NP; from 3 to 5 TAs per NP; the ratio of TA to PS is 2.5 to 1 and greater; the ratio of TA to PS is 3 to 1 and greater; the ratio of TA to PS is 5 to 1 and greater; having 1 free arm; having 2 free arms; having 3 free arms; and having 4 free arms.

Example 14

Illumination for the embodiments of the present nanocompositions and PDT are as follows. The source of light may include but is not limited to LED array, continuous laser light (diode or other), chopped laser light (ie shorter time on at a higher power, then off)—this allows a deeper penetration through the skin while delivering the same power in the same time but not thermally damaging the skin/tissue)—likely preferable for through the skin applications. Some examples of energy of the source of light may include but are not limited to, less that 1 KJ/cm2 (total energy as this is the thermal limit of tissue), in a range of 150-400 J/cm2. In some embodiments, the energy from the source of light may be delivered as a continuous illumination (LED, CW) or could be pulsed at a higher power to gain deeper penetration.

Potential sites of illumination may be internal, through the skin, external to the body, or reacting fluids for later use. For example, an internal site may include y "intubation"—bladder, lung, stomach, esophagus, etc. Additionally, it may be administered by surgical insertion of a catheter (usually referred to as interstitial PDT or iPDT) and/or through the surgical insertion of a RF activated LED at the required site. Light could be directly generated at the [internal] site by Examples of potential sites of illumination through the skin at sites where the skin/structure is thin to allow transmission of light, such as but not limited to, ear lobe, fingertip/finger, toe, wrist, and/or any area of the skin where a useful dose of light can be delivered [to the desired body fluid]. Other examples may be external to the body (e.g., through a shunt) which may likely be a venal shunt not an arterial one. This would be the illumination of the body fluid (blood) in a device before the fluid is returned to the body. Another site of illumination may be through retained fluids for later use (ie whole blood, Plasma for transfusion), direct illumination—either in the "bag" or as being transferred to the bag, or [NB the active NP would be added after removal from the body].

Discussed below are Devices/geometries of delivery of the light through internally transmission, through the skin, ex-vivo, and/or external/retained fluids. An internal transmission may include catheters/laparoscopy etc., variety of diffuser tips (as per current PDT and iPDT practice), such as, cylindrical, through a balloon, and/or from the tip (aka a flashlight). Additionally, internal transmission may be performed through the surgical insertion of a RF activated LED at the required site. Light could be directly generated at the [internal] site by application of localized RF energy Delivery thought he skin such as ear lobe/fingertip etc. may be performed by a wearable "clip" (such as a pulseOX meter) that either es self-contained, including a power source and a light source or light source is either a diode laser or an LED of the appropriate power and wavelength. Additionally, delivery may simply be a method of positioning and locating an external light source over the desired area-connected via a light transmission [optical fiber] system. Other methods and systems may include a band/wrap for the wrist/ankle etc. providing a useful does of light can be delivered.

In examples, delivery may be performed ex-vivo (most likely an in-line venous shunt, but could be arterial)—note that this could be multiple veins it does not just have to a single one. For example, a co-continuous light source wrapped around a transparent tube—dimensions to be defined—but perhaps 30 cm-100 cm, an illuminated chamber—through which the fluid is circulated in a transparent "Coil" [vertical or horizontal]—longer surface area, a "cell" wherein the blood is flowing, that provides a high surface area and short illumination path length to maximize light power delivery—think two parallel plates maybe 1 m2 or as series of cells that are illuminated, and/or in both the previous cases this illumination is likely via an LED array.

Deliver through external/retained fluids (transfusion) may be stated earlier the NP is added to the fluid after removal and treated prior to storage. In examples, whole blood may be used but may require a device to flow the blood through prior to "bagging"—as there will need to be a sufficiently short path length to get useful power into the whole blood. In other examples, plasma may be used, the methods for whole blood described above may be used although the useful transmission length is longer (as the RBC's are gone). Another form is through NB, however as the NP would remain in the blood and plasma until transfusion.

It should be understood that the use of headings in this specification is for the purpose of clarity, and is not limiting in any way. Thus, the processes and disclosures described under a heading should be read in context with the entirely of this specification, including the various examples. The use of headings in this specification should not limit the scope of protection afford the present inventions.

It is noted that there is no requirement to provide or address the theory underlying the novel and groundbreaking processes, materials, performance or other beneficial features and properties that are the subject of, or associated with, embodiments of the present inventions. Nevertheless, various theories are provided in this specification to further advance the art in this area. The theories put forth in this specification, and unless expressly stated otherwise, in no way limit, restrict or narrow the scope of protection to be afforded the claimed inventions. These theories many not be required or practiced to utilize the present inventions. It is further understood that the present inventions may lead to new, and heretofore unknown theories to explain the function-features of embodiments of the methods, articles, materials, devices and system of the present inventions; and such later developed theories shall not limit the scope of protection afforded the present inventions.

The various embodiments of systems, therapies, processes, compositions, applications, and materials set forth in this specification may be used for various other fields and for various other activities, uses and embodiments. Additionally, these embodiments, for example, may be used with: existing systems, therapies, processes, compositions, applications, and materials; may be used with systems, therapies, processes, compositions, applications, and materials that may be developed in the future; and with systems, therapies, processes, compositions, applications, and materials that may be modified, in-part, based on the teachings of this specification. Further, the various embodiments and examples set forth in this specification may be used with each other, in whole or in part, and in different and various combinations. Thus, for example, the configurations provided in the various embodiments of this specification may be used with each other. For example, the components of an embodiment having A, A' and B and the components of an embodiment having A", C and D can be used with each other in various combination, e.g., A, C, D, and A. A" C and D, etc., in accordance with the teaching of this specification. The scope of protection afforded the present inventions should not be limited to a particular embodiment, example, configuration or arrangement that is set forth in a particular embodiment, example, or in an embodiment in a particular figure.

The invention may be embodied in other forms than those specifically disclosed herein without departing from its spirit or essential characteristics. The described embodiments are to be considered in all respects only as illustrative and not restrictive.

What is claimed is:

1. A system comprising:

a first composition comprising:

a plurality of nanoparticles, the nanoparticles comprising an 8-arm PEG core;

wherein the 8-arm PEG core is substituted with at least a photosensitizer (PS) that is directly linked to the 8-arm PEG core;

wherein at least three arms of the 8-arm PEG core are unsubstituted;

wherein the 8-arm PEG core contains 1-2 PS per 8-arm PEG core; and wherein the 8-arm PEG core has a weight of at least about 10 kDa; and a second composition comprising:

a plurality of agents for targeted delivery of the plurality of nanoparticles of the first composition.

2. The system of claim 1, wherein the 8-arm PEG core is further substituted with at least a targeting agent (TA) that is directly linked to the 8-arm PEG core.

3. The system of claim 1, wherein the agents for targeted delivery are selected from the group consisting of a protein, a peptide, an enzyme substrate, a hormone, an antibody, an antigen, a hapten, an avidin, a streptavidin, biotin, a carbohydrate, an oligosaccharide, a polysaccharide, a nucleic acid, a deoxy nucleic acid, a fragment of DNA, a fragment of RNA, nucleotide triphosphates, acyclo terminator triphosphates, peptide nucleic acid (PNA) biomolecules, and combinations thereof.

4. The system of claim 1, wherein the photosensitizer (PS) is IR700.

5. The system of claim 2, wherein the targeting agent (TA) is an RGD peptide.

6. The system of claim 2, wherein the targeting agent (TA) is iRGD.

7. The system of claim 1, wherein the photosensitizer is a phthalocyanine dye.

8. The system of claim 1, wherein the direct link is a covalent link.

9. The system of claim 2, wherein the direct link is a covalent link.

10. The system of claim 1, further comprising at least an additive directly linked to the 8-arm PEG core and the additive is selected from the group consisting of therapeutic agents, diagnostic agents, theranostic agents, and combinations thereof.

11. The system of claim 1, wherein the nanoparticles have a hydrodynamic diameter of 25 nm or less.

12. A method of treating a cardiac, oncologic, bariatric, or dermatologic condition in a subject in need thereof, the method comprising the steps of:

(1) administering a first and a second composition to the subject, the first composition comprising:

a plurality of nanoparticles, the nanoparticles comprising an 8-arm PEG core;

wherein the 8-arm PEG core is substituted with at least a photosensitizer (PS) that is directly linked to the 8-arm PEG core;

wherein at least three arms of the 8-arm PEG core are unsubstituted;

wherein the 8-arm PEG core contains 1-2 PS per 8-arm PEG core; and wherein the 8-arm PEG core has a weight of at least about 10 kDa; and the second composition comprising:

a plurality of agents for targeted delivery of the plurality of nanoparticles of the first composition;

(2) allowing a period of time for the first and the second compositions to accumulate in a target tissue of the subject;

(3) imaging the plurality of nanoparticles of the first composition following step (2)

wherein the imaging is able to visualize the target tissue and optionally may be used to analyze the size, shape, position, and composition of the target tissue; and (4) optionally administering a light dosage to activate the PS in the first composition.

13. The method of claim 12, wherein the 8-arm PEG core is further substituted with at least a targeting agent (TA) that is directly linked to the 8-arm PEG core.

14. The method of claim 12, wherein the agents for targeted delivery are selected from the group consisting of a protein, a peptide, an enzyme substrate, a hormone, an antibody, an antigen, a hapten, an avidin, a streptavidin, biotin, a carbohydrate, an oligosaccharide, a polysaccharide, a nucleic acid, a deoxy nucleic acid, a fragment of DNA, a fragment of RNA, nucleotide triphosphates, acyclo terminator triphosphates, peptide nucleic acid (PNA) biomolecules, and combinations thereof.

15. The method of claim 12, wherein the light dosage kills the target tissue.

16. The method of claim 12, wherein the first and the second composition are administered via intravenous injection.

17. The method of claim 12, wherein the light dosage is less than 1 $KJ/cm^2$, and wherein the light source is selected from an LED, a continuous laser, a pulsed laser, or combinations thereof.

18. The method of claim 12, wherein the light dosage is between 100 and 400 $J/cm^2$.

19. The method of claim 12, wherein the photosensitizer (PS) is a phthalocyanine dye.

20. The method of claim 12, wherein the photosensitizer (PS) is IR700.

21. The method of claim 12, wherein the targeting agent (TA) is an RGD peptide.

22. The method of claim 12, wherein the targeting agent (TA) is iRGD.

* * * * *